(12) United States Patent
Thornton

(10) Patent No.: US 8,316,857 B2
(45) Date of Patent: Nov. 27, 2012

(54) ORAL APPLIANCE FOR TREATING A BREATHING CONDITION

(75) Inventor: W. Keith Thornton, Dallas, TX (US)

(73) Assignee: AirWay Technologies, LLC, Carrollton, TX (US)

( * ) Notice: Subject to any disclaimer, the term of this patent is extended or adjusted under 35 U.S.C. 154(b) by 0 days.

(21) Appl. No.: 12/795,343

(22) Filed: Jun. 7, 2010

(65) Prior Publication Data

US 2010/0263676 A1   Oct. 21, 2010

Related U.S. Application Data

(63) Continuation-in-part of application No. 11/278,918, filed on Apr. 6, 2006, now Pat. No. 7,748,386.

(51) Int. Cl.
*A61F 5/37* (2006.01)
*A61F 13/00* (2006.01)
*A61F 11/00* (2006.01)
*A61C 5/14* (2006.01)
*A61C 3/00* (2006.01)
*A61C 9/00* (2006.01)
*A61C 19/04* (2006.01)
*A61C 5/00* (2006.01)

(52) U.S. Cl. ........ 128/848; 128/846; 128/857; 128/859; 128/861; 128/862; 433/6; 433/37; 433/41; 433/68; 433/140; 602/902

(58) Field of Classification Search ............... 128/846, 128/848, 857, 861, 862, 859; 602/902; 433/6, 433/37, 41, 68, 69, 140
See application file for complete search history.

(56) References Cited

U.S. PATENT DOCUMENTS 690,663 A   1/1902   Pratt
(Continued)

FOREIGN PATENT DOCUMENTS

DE   2 320 501   11/1974
(Continued)

OTHER PUBLICATIONS

Mayo Clinic Health Letter; Reliable Information for a Healthier Life; *Snoring: Laser Surgery Joins Battle to Restore Peace and Quiet*; vol. 13, No. 7, 8 pages, Jul. 1995.

(Continued)

*Primary Examiner* — Patricia Bianco
*Assistant Examiner* — Brandon L Jackson
(74) *Attorney, Agent, or Firm* — Baker Botts L.L.P.

(57) ABSTRACT

An apparatus for use in treating a breathing condition includes a first dental arch, a second dental arch, two bodies coupled to the first dental arch, and two receivers coupled to the second dental arch. The first dental arch is configured to receive at least some of a wearer's teeth. The second dental arch is configured to receive at least some of a wearer's teeth. Each body includes a front stop, a rear stop, a threaded member, and a hook. The threaded member is configured to be coupled between the front stop and rear stop of the body and configured to rotate relative to the body. The hook comprises a threaded passage configured to engage the threaded member, and an arm configured to engage a second dental arch. The hook is configured to travel between the front stop and rear stop of the body in response to rotational adjustment of the threaded member to adjust the lower dental arch relative to the upper dental arch. Each receiver comprises a first rail configured to engage the arm of the hook of a respective one of the two bodies. The first rail is disposed exterior to an internal area defined by a span of the second dental arch. The two receivers are entirely disposed, with respect to each other, on opposite sides of a plane bisecting left and right halves of the second dental arch.

22 Claims, 17 Drawing Sheets

U.S. PATENT DOCUMENTS

| | | |
|---|---|---|
| 746,869 A | 12/1903 | Moulton |
| 774,446 A | 11/1904 | Moulton |
| 885,196 A | 4/1908 | Steil |
| 893,213 A | 7/1908 | Whiteway |
| 955,562 A | 4/1910 | Thomas |
| 996,783 A | 7/1911 | Moreau |
| 1,076,534 A | 10/1913 | Wallen |
| 1,146,264 A | 7/1915 | Kelly |
| 1,483,694 A | 2/1924 | Stukey |
| 1,592,345 A | 7/1926 | Drager |
| 1,649,664 A | 11/1927 | Carter |
| 1,674,336 A | 6/1928 | King |
| 1,675,202 A | 6/1928 | Warne |
| 1,679,748 A | 8/1928 | Stratton |
| 2,171,695 A | 9/1939 | Harper |
| 2,178,128 A | 10/1939 | Waite |
| 2,424,533 A | 7/1947 | Faires |
| 2,505,028 A | 4/1950 | Boeger |
| 2,521,039 A | 9/1950 | Carpenter |
| 2,521,084 A | 9/1950 | Oberto |
| 2,531,222 A | 11/1950 | Kesling |
| 2,574,623 A | 11/1951 | Clyde |
| 2,590,118 A | 3/1952 | Oddo, Jr. |
| 2,627,268 A | 2/1953 | Leppich |
| 2,833,278 A | 5/1958 | Ross |
| 2,867,212 A | 1/1959 | Nunn, Jr. |
| 2,882,893 A | 4/1959 | Godfroy |
| 3,037,501 A | 6/1962 | Miller |
| 3,064,354 A | 11/1962 | Pos |
| 3,107,668 A | 10/1963 | Thompson |
| 3,124,129 A | 3/1964 | Grossberg |
| 3,132,647 A | 5/1964 | Corniello |
| 3,219,033 A | 11/1965 | Wallshein |
| 3,277,892 A | 10/1966 | Tepper |
| 3,312,216 A | 4/1967 | Wallshein |
| 3,321,832 A | 5/1967 | Weisberg |
| 3,360,860 A | 1/1968 | Roland |
| 3,434,470 A | 3/1969 | Strickland |
| 3,457,916 A | 7/1969 | Wolicki |
| 3,513,838 A | 5/1970 | Foderick et al. |
| 3,522,805 A | 8/1970 | Wallshein |
| 3,690,004 A | 9/1972 | Frush |
| 3,854,208 A | 12/1974 | Arant |
| 3,864,832 A | 2/1975 | Carlson |
| 3,871,370 A | 3/1975 | McDonald |
| 3,882,601 A | 5/1975 | Jahn |
| 3,884,226 A | 5/1975 | Tepper |
| 4,016,650 A | 4/1977 | Leusner et al. |
| 4,026,024 A | 5/1977 | Tradowsky |
| 4,114,614 A | 9/1978 | Kesling |
| 4,169,473 A | 10/1979 | Samelson |
| 4,182,312 A | 1/1980 | Mushabac |
| 4,227,877 A | 10/1980 | Tureaud et al. |
| 4,258,710 A | 3/1981 | Reber |
| 4,289,127 A | 9/1981 | Nelson |
| 4,304,227 A | 12/1981 | Samelson |
| 4,376,628 A | 3/1983 | Aardse |
| 4,382,783 A | 5/1983 | Rosenberg |
| 4,419,992 A | 12/1983 | Chorbajian |
| 4,433,956 A | 2/1984 | Witzig |
| 4,439,147 A | 3/1984 | Magill et al. |
| 4,439,149 A | 3/1984 | Devincenzo |
| 4,454,090 A | 6/1984 | Saumell |
| 4,495,945 A | 1/1985 | Liegner |
| 4,505,672 A | 3/1985 | Kurz |
| 4,530,662 A | 7/1985 | Andersson et al. |
| 4,553,549 A | 11/1985 | Pope et al. |
| 4,568,280 A | 2/1986 | Ahlin |
| 4,569,342 A | 2/1986 | von Nostitz |
| 4,593,686 A | 6/1986 | Lloyd et al. |
| 4,602,905 A | 7/1986 | O'Keefe, III |
| 4,639,220 A | 1/1987 | Nara et al. |
| 4,668,188 A | 5/1987 | Wolfenson et al. |
| 4,669,459 A | 6/1987 | Spiewak et al. |
| 4,676,240 A | 6/1987 | Gardy |
| 4,715,368 A | 12/1987 | George |
| 4,741,696 A | 5/1988 | Cetlin |
| 4,773,853 A | 9/1988 | Kussick |
| 4,784,123 A | 11/1988 | Robeson |
| 4,799,500 A | 1/1989 | Newbury |
| 4,858,605 A | 8/1989 | Levy |
| 4,862,903 A | 9/1989 | Campbell |
| 4,892,478 A | 1/1990 | Tateosian et al. |
| 4,901,737 A | 2/1990 | Toone |
| 4,932,867 A | 6/1990 | Ueno |
| 4,955,393 A | 9/1990 | Adell |
| RE33,442 E | 11/1990 | George |
| 5,003,994 A | 4/1991 | Cook |
| 5,011,407 A | 4/1991 | Pelerin |
| 5,018,533 A | 5/1991 | Hawkins |
| 5,026,278 A | 6/1991 | Oxman et al. |
| 5,028,232 A | 7/1991 | Snow |
| 5,040,976 A | 8/1991 | Ubel, III et al. |
| 5,042,506 A | 8/1991 | Liberati |
| 5,046,512 A | 9/1991 | Murchie |
| 5,052,409 A | 10/1991 | Tepper |
| 5,055,039 A | 10/1991 | Abbatte et al. |
| 5,056,534 A | 10/1991 | Wright |
| 5,064,371 A | 11/1991 | Smeltzer |
| 5,066,231 A | 11/1991 | Oxman et al. |
| 5,078,600 A | 1/1992 | Austin |
| 5,092,346 A | 3/1992 | Hays et al. |
| 5,103,838 A | 4/1992 | Yousif |
| 5,112,225 A | 5/1992 | Diesso |
| 5,117,816 A | 6/1992 | Shapiro et al. |
| 5,154,184 A | 10/1992 | Alvarez |
| 5,154,609 A | 10/1992 | George |
| 5,183,057 A | 2/1993 | Syrop et al. |
| 5,188,529 A | 2/1993 | Lüth |
| 5,190,457 A | 3/1993 | Schreinemakers |
| 5,213,498 A | 5/1993 | Pelerin |
| 5,265,595 A | 11/1993 | Rudolph |
| 5,267,862 A | 12/1993 | Parker |
| 5,277,202 A | 1/1994 | Hays |
| 5,284,161 A | 2/1994 | Karell |
| 5,313,960 A | 5/1994 | Tomasi |
| 5,316,020 A | 5/1994 | Truffer |
| 5,320,533 A | 6/1994 | Lee |
| 5,336,086 A | 8/1994 | Simmen et al. |
| 5,365,945 A | 11/1994 | Halstrom |
| 5,370,533 A | 12/1994 | Bushnell |
| 5,373,859 A | 12/1994 | Forney |
| 5,409,017 A | 4/1995 | Lowe |
| 5,415,544 A | 5/1995 | Oxman et al. |
| 5,427,117 A | 6/1995 | Thornton |
| 5,474,060 A | 12/1995 | Evans |
| 5,499,633 A | 3/1996 | Fenton |
| 5,503,552 A | 4/1996 | Diesso |
| 5,537,994 A | 7/1996 | Thornton |
| 5,551,872 A | 9/1996 | Mena |
| 5,562,449 A | 10/1996 | Jacobs et al. |
| 5,566,683 A | 10/1996 | Thornton |
| 5,570,704 A | 11/1996 | Buzzard et al. |
| 5,582,517 A | 12/1996 | Adell |
| 5,678,567 A | 10/1997 | Thornton et al. |
| 5,681,164 A | 10/1997 | Bass |
| 5,718,244 A | 2/1998 | Thornton |
| 5,720,302 A | 2/1998 | Belfer |
| 5,755,219 A | 5/1998 | Thornton |
| 5,807,100 A | 9/1998 | Thornton |
| 5,829,441 A | 11/1998 | Kidd et al. |
| 5,846,082 A | 12/1998 | Thornton |
| 5,891,372 A | 4/1999 | Besset et al. |
| 5,954,048 A | 9/1999 | Thornton |
| 5,983,892 A | 11/1999 | Thornton |
| 6,012,919 A | 1/2000 | Cross, III |
| 6,083,442 A | 7/2000 | Gabilly |
| 6,109,265 A | 8/2000 | Frantz et al. |
| 6,155,262 A | 12/2000 | Thornton et al. |
| 6,209,542 B1 | 4/2001 | Thornton |
| 6,247,926 B1 | 6/2001 | Thornton |
| 6,305,376 B1 | 10/2001 | Thornton |
| 6,318,997 B1 | 11/2001 | Mayweather |
| 6,325,064 B1 | 12/2001 | Thornton |
| 6,374,824 B1 | 4/2002 | Thornton |
| 6,405,729 B1 | 6/2002 | Thornton |
| 6,450,167 B1 * | 9/2002 | David et al. ............ 128/848 |

| | | | |
|---|---|---|---|
| 6,464,924 B1 | 10/2002 | Thornton | |
| 6,516,805 B1 | 2/2003 | Thornton | |
| 6,536,439 B1 | 3/2003 | Palmisano | |
| 6,571,798 B1 | 6/2003 | Thornton | |
| 6,604,527 B1 | 8/2003 | Palmisano | |
| 6,675,802 B1 | 1/2004 | Thornton | |
| 6,758,212 B2 | 7/2004 | Swann | |
| 6,845,774 B2 | 1/2005 | Gaskell | |
| 6,877,513 B2 | 4/2005 | Scarberry et al. | |
| 7,174,895 B2 | 2/2007 | Thornton et al. | |
| 7,597,103 B2 | 10/2009 | Thornton et al. | |
| 7,650,885 B2 | 1/2010 | Paoluccio et al. | |
| 7,677,889 B2 | 3/2010 | Thornton | |
| 7,721,741 B2 | 5/2010 | Thornton | |
| 7,748,386 B2 | 7/2010 | Thornton | |
| 7,823,590 B2 | 11/2010 | Bibi et al. | |
| 7,832,403 B2 | 11/2010 | Halstrom | |
| 7,909,035 B2 | 3/2011 | Thornton | |
| 8,020,276 B2 | 9/2011 | Thornton | |
| 2002/0000230 A1 | 1/2002 | Gaskell | |
| 2002/0139366 A1 | 10/2002 | Gaschke | |
| 2003/0217753 A1 | 11/2003 | Thornton | |
| 2003/0234022 A1 | 12/2003 | Belfer | |
| 2004/0079374 A1 | 4/2004 | Thornton | |
| 2004/0226563 A1 | 11/2004 | Xu et al. | |
| 2004/0237965 A1 | 12/2004 | Bibi et al. | |
| 2005/0028827 A1 | 2/2005 | Halstrom | |
| 2005/0034733 A1 | 2/2005 | Liddle et al. | |
| 2005/0268914 A1 | 12/2005 | Paoluccio et al. | |
| 2007/0125388 A1 | 6/2007 | Thornton et al. | |
| 2007/0235037 A1 | 10/2007 | Thornton | |
| 2008/0006273 A1 | 1/2008 | Thornton | |
| 2008/0006274 A1 | 1/2008 | Thornton | |
| 2008/0032256 A1 | 2/2008 | Thornton | |
| 2008/0127984 A1 | 6/2008 | Thornton | |
| 2008/0295850 A1 | 12/2008 | Lesniak | |
| 2009/0130624 A1 | 5/2009 | Sun et al. | |
| 2010/0065067 A1* | 3/2010 | Lee | 128/848 |
| 2011/0168187 A1* | 7/2011 | Nelissen | 128/848 |

FOREIGN PATENT DOCUMENTS

| | | |
|---|---|---|
| DE | 29506512.5 | 7/1995 |
| EP | 0 312 368 A1 | 4/1989 |
| EP | 0 359 135 A1 | 3/1990 |
| GB | 1 569 129 | 6/1980 |
| GB | 2 072 567 A | 10/1981 |
| WO | WO 91/12777 | 9/1991 |
| WO | WO 97/25010 | 7/1997 |
| WO | WO 98/26736 | 6/1998 |
| WO | WO 98/46177 | 10/1998 |

OTHER PUBLICATIONS

Photocopies of 2-piece dental device manufactured by Currie-Gibson Dental Lboratory, Inc., prior to Apr. 13, 1993, 5 pages, Prior to Apr. 13, 2001.

Farrar, et al, *A Clinical Outline of Temporomandibular Joint Diagnosis and Treatment*, Normandie Study Group for TMJ Dysfunction, 3 pages, 1983.

Professional Positioners; *Dedicated to Excellence* brochure, 3 pages.

Great Lakes Orthodontics, Ltd.; *Nocturnal Airway Patency Applicance*; 2 pages.

Schmidt-Nowara, et al.; An American Sleep Disorders Association Review; *Oral Appliances for the Treatment of Snoring and Obstructive Sleep Apnea: A Review*; pp. 501-510, 1995.

George, Peter; *Treatment of Snoring and Obstructive Sleep Apnea with a Dental Device*; 5 pages, Jul.-Aug. 1993.

Database WOI, Section PQ, Week 9039, Derwent Publications, Ltd., London, GB; XP-002116355 Abstract—*Surgical Mouth Air Duct*; 1 page, Dec. 15, 1989.

PCT Notification of Transmittal of The International Search Report or the Declaration for International Application No. PCT/US97/08708, 4 pages, Aug. 12, 1997.

PCT Invitation to Pay Additional Fees for International Application No. PCT/US03/13705, 6 pages, Oct. 10, 2003.

PCT, Notification of Transmittal of the International Search Report and the Written Opinion of the International Searching Authority, or the Declaration, PCT/US07/02736, 10 pages, Date Mailed: Nov. 26, 2007.

Personally Moulded Sleep Apnea Masks, http://;web.archive.org/web/20030618145716/ www.sleepapneamasks.com.au/default.asp, downloaded Aug. 17, 2009 (2 pages).

European Patent Office, Application No. 03 809 555.0-125, Applicant: W. Keith Thornton, 3 pages, dated Feb. 23, 2010; 4 pages.

PCT, Notification of Transmittal of the International Search Report and the Written Opinion of the International Searching Authority, or the Declaration, International Application No. PCT/US2011/039231, filed Jun. 6, 2011 (11 pgs).

PCT, Notification of Transmittal of the International Search Report and the Written Opinion of the International Searching Authority, or the Declaration, PCT/US2010/051136, 10 pages, Mar. 4, 2011.

Japanese Patent Office re patent application 2004-500750, mailed Oct. 14, 2008.

PCT Intl. Searching Authority, Invitation to pay Add'l Fees, Re PCT/US2012/028885 mailed May 30, 2012 (0306 Foreign).

PCT Intl. Searching Authority, Invitation to pay Add'l Fees, Re PCT/US2012/032407 mailed May 30, 2012.

Canadian IPO patent application No. 2,502,280 dated Feb. 23, 2010.

Craig, William H., et al.; "Skeletal class II treatment with the Chateau appliance," The Journal of Pedondontics (vol. 11:120); pp. 120-138, 1987.

Samuel T. Kuna, M.D., et al., "Effect of Progressive Mandibular Advancement on Pharyngeal Airway Size in Anesthetized Adults," National Institute of Health; NIH Public Access Author Manuscript; Published Oct. 2008; Anesthesiology; 109(4); 16 pages.

Australian Office Action re: Pat. App. # 2007243957; dated Mar. 9, 2012; 3 pages.

PCT Notification of Transmittal of the International Search Report and the Written Opinion of the International Searching Authority, or the Declaration; mailed Jul. 13, 2012; International app No. PCT/US2012/032407; 18 pages.

* cited by examiner

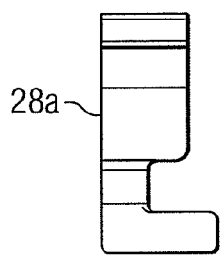
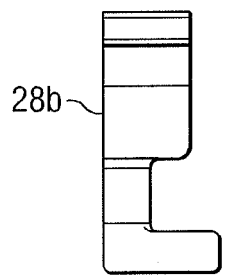
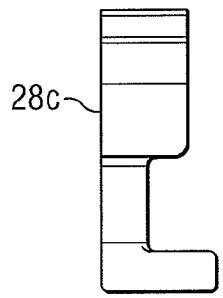
FIG. 6A        FIG. 6B        FIG. 6C
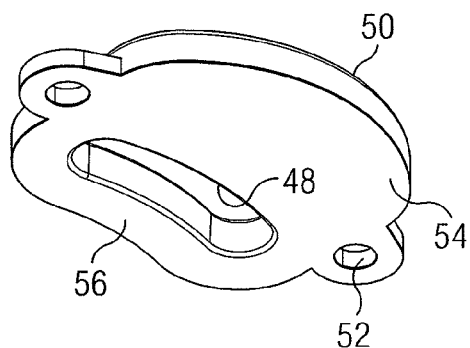
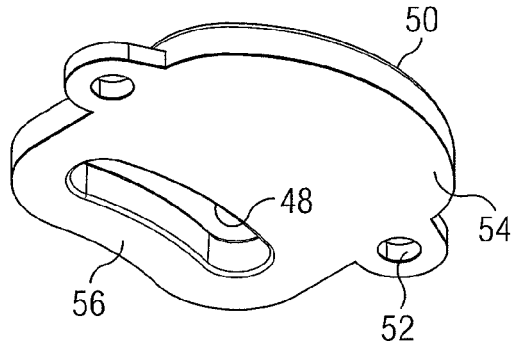
FIG. 7A        FIG. 7B
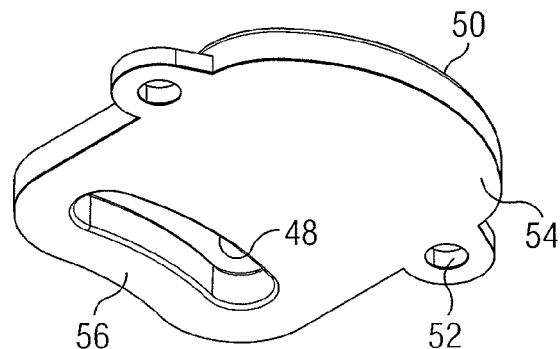
FIG. 7C

ORAL APPLIANCE FOR TREATING A BREATHING CONDITION

RELATED APPLICATIONS

This application claims the benefit under 35 U.S.C. §120 as a continuation-in-part of Ser. No. 11/278,918, now U.S. Pat. No. 7,748,386 filed Apr. 6, 2006, which is incorporated herein by reference.

TECHNICAL FIELD OF THE INVENTION

This invention relates generally to oral appliances, and more particularly to an oral appliance for use in treating a breathing condition.

BACKGROUND

Many people experience breathing problems, which may result in difficulty sleeping, in snoring, or in other more serious conditions such as obstructive sleep apnea. One treatment for such breathing disorders involves the use of devices that are inserted into a user's mouth for extending the user's lower jaw forward. These devices open the airway (i.e., breathing passageway) more fully to allow easier breathing through the nose and mouth. Certain of these devices include upper and lower arches that are connected together using a mechanism that may be adjusted to pull the lower arch, and thus the user's lower jaw, forward to open the airway more fully.

SUMMARY OF THE INVENTION

Oral appliances and methods according to the present invention may reduce or eliminate certain disadvantages and problems associated with previous devices and methods for improving breathing.

In one embodiment, an apparatus for use in treating a breathing condition includes a first dental arch, a second dental arch, two bodies coupled to the first dental arch, and two receivers coupled to the second dental arch. The first dental arch is configured to receive at least some of a wearer's teeth. The second dental arch is configured to receive at least some of a wearer's teeth. Each body includes a front stop, a rear stop, a threaded member, and a hook. The threaded member is configured to be coupled between the front stop and rear stop of the body and configured to rotate relative to the body. The hook comprises a threaded passage configured to engage the threaded member, and an arm configured to engage a second dental arch. The hook is configured to travel between the front stop and rear stop of the body in response to rotational adjustment of the threaded member to adjust the lower dental arch relative to the upper dental arch. Each receiver comprises a first rail configured to engage the arm of the hook of a respective one of the two bodies. The first rail is disposed exterior to an internal area defined by a span of the second dental arch. The two receivers are entirely disposed, with respect to each other, on opposite sides of a plane bisecting left and right halves of the second dental arch.

Certain embodiments of the present invention may provide one or more technical advantages. For example, certain embodiments may provide for precise positioning of the lower jaw as well as positioning of one or more devices relative to the upper dentition. As another example, certain embodiments may provide for improved positioning of the lower arch relative to the upper arch for particular users. Certain embodiments may provide for improved positioning or coupling of an oral appliance to a breathing device. Certain embodiments may provide some, none, or all of these advantages. Certain embodiments may provide one or more other technical advantages, one or more of which may be readily apparent to those skilled in the art from the figures, description, and claims included herein.

BRIEF DESCRIPTION OF THE DRAWINGS

For a more complete understanding of the present invention and at least some of its advantages, reference is now made to the following description taken in conjunction with the accompanying drawings, in which:

FIGS. 6A through 6C illustrate example hooks with varying lengths, for use with an example adjustment mechanism;

FIGS. 7A through 7C illustrate example receivers with varying dimensions;

DESCRIPTION OF EXAMPLE EMBODIMENTS

Figure 1:
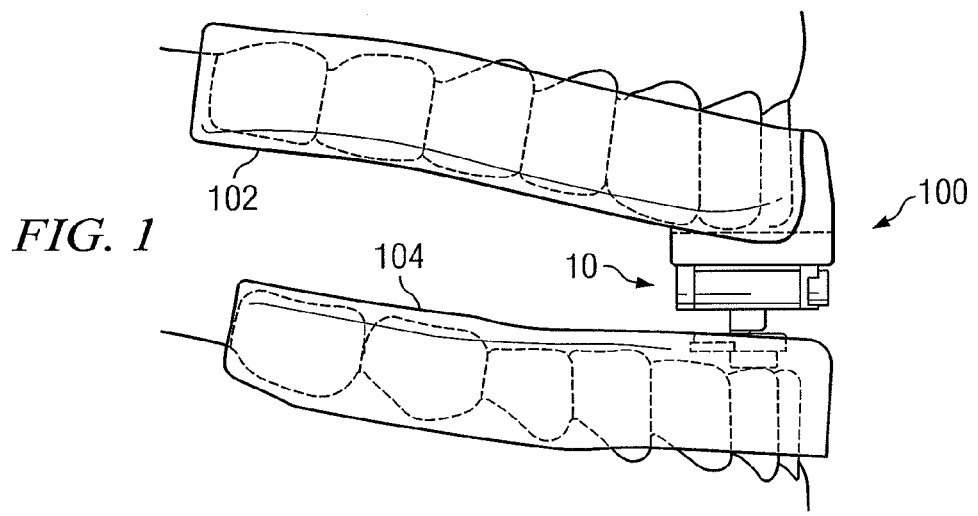
FIG. 1 illustrates an example oral appliance for improving a user's breathing.
Figure 2A:
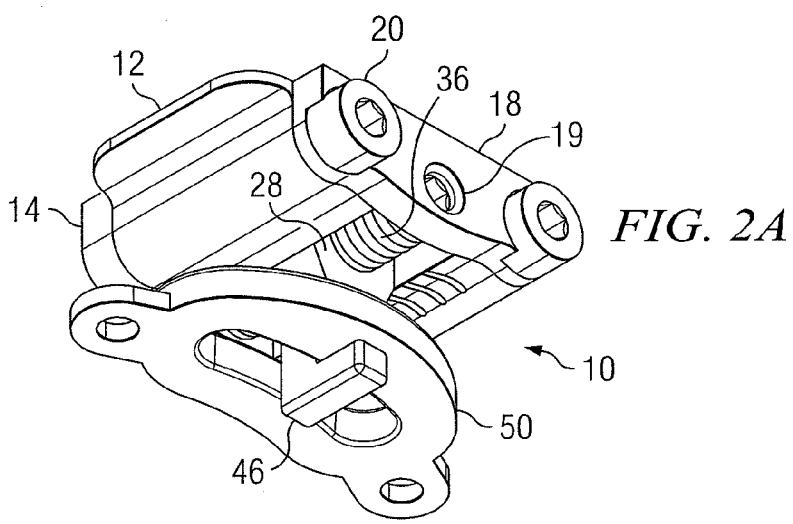
FIGS. 2A through 5B illustrate an example adjustment mechanism.
Figure 2B:
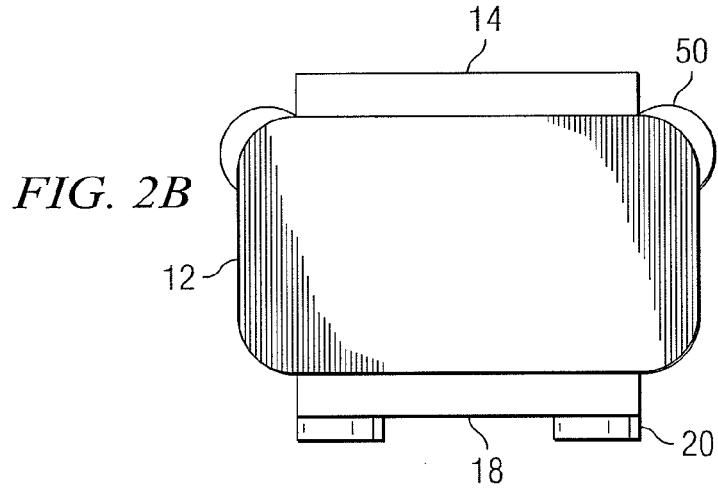
Figure 2C:
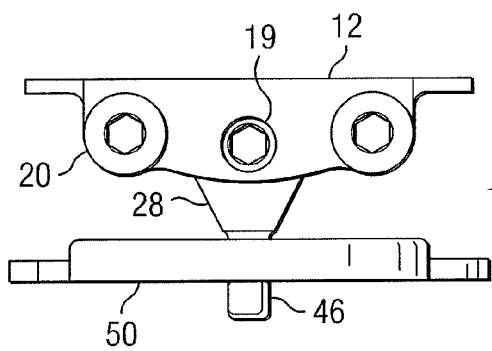
Figure 2D:
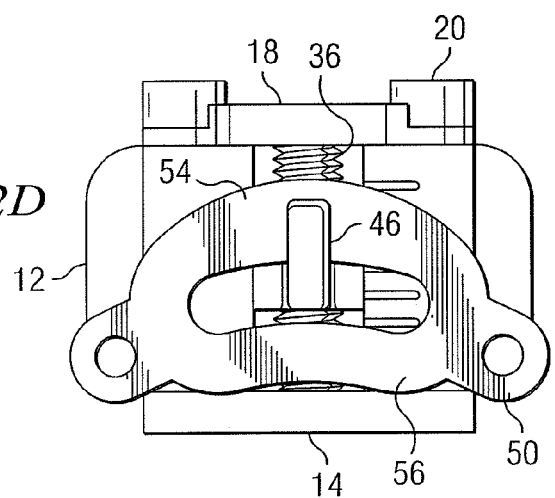
Figure 3:
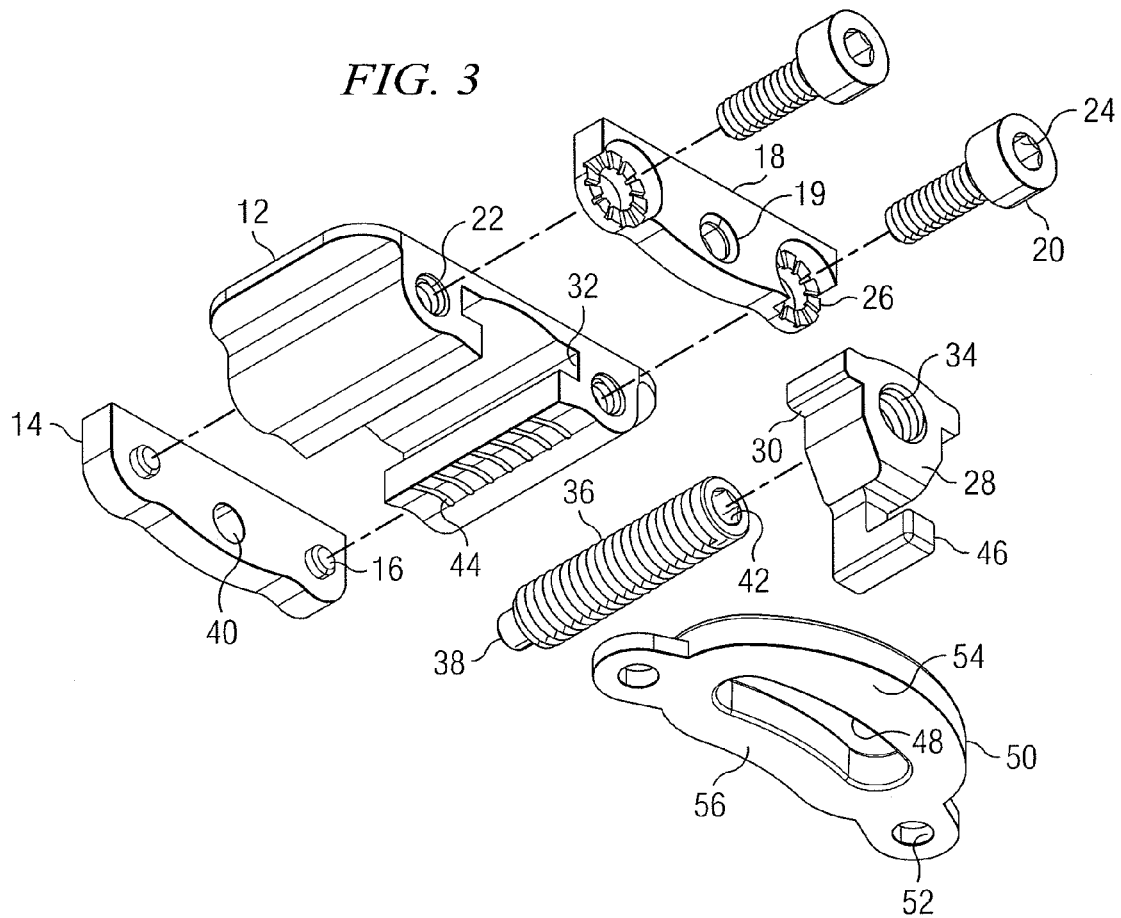
Figure 4A:
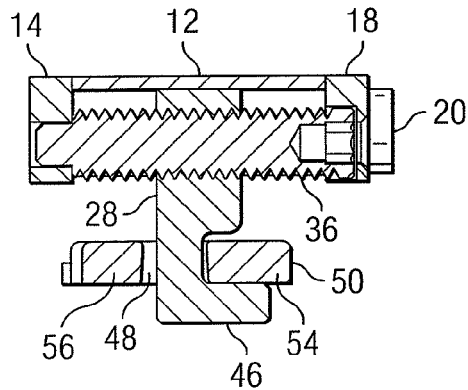
Figure 4B:
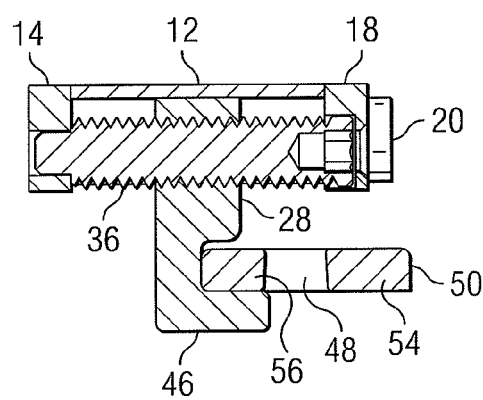
Figure 5A:
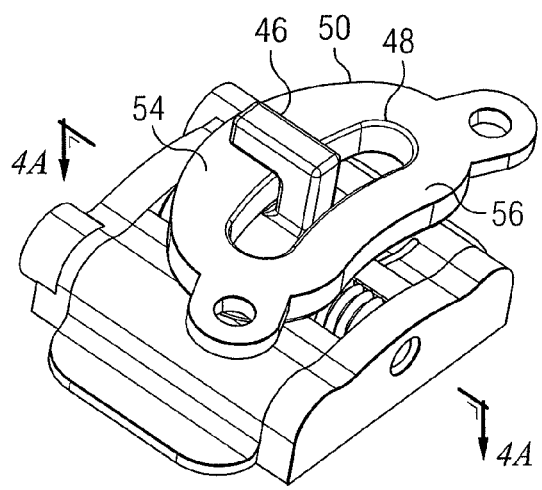
Figure 5B:
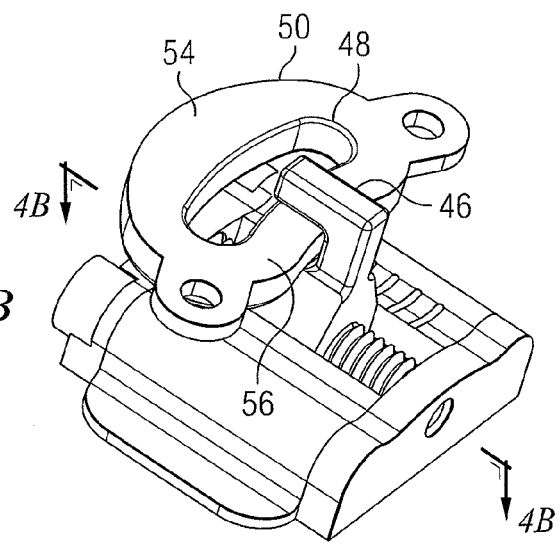
Figure 8A:
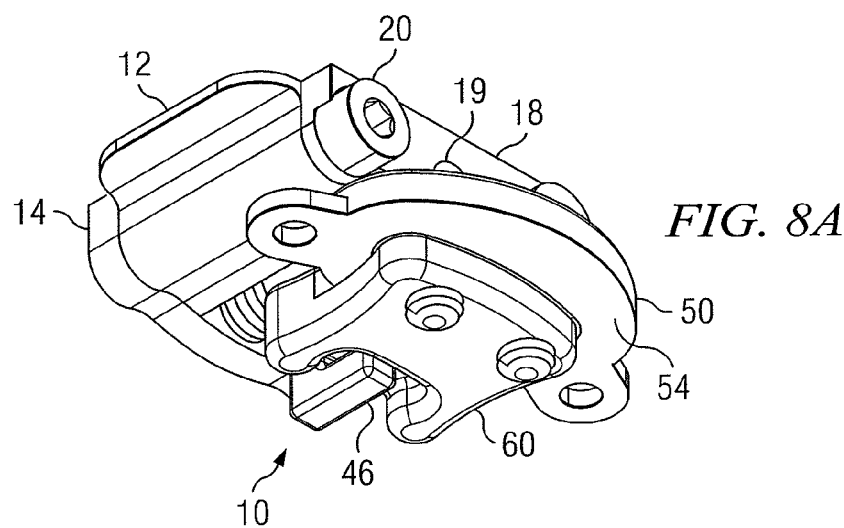
FIGS. 8A through 10 illustrate an example adjustment mechanism utilizing an example extender.
Figure 8B:
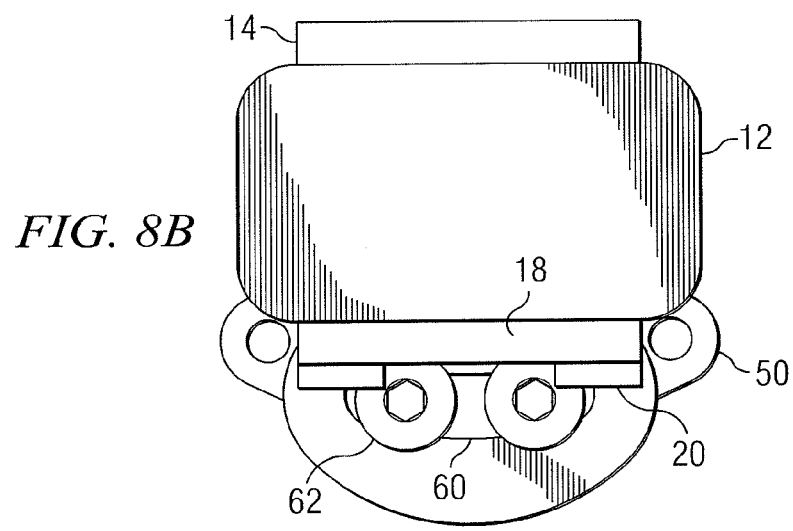
Figure 8C:
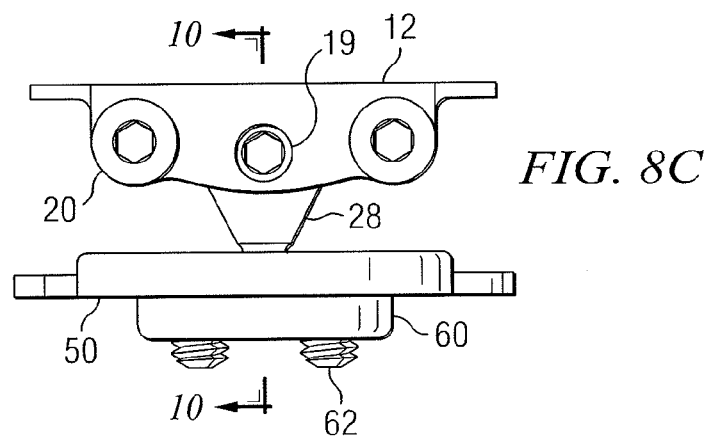
Figure 8D:
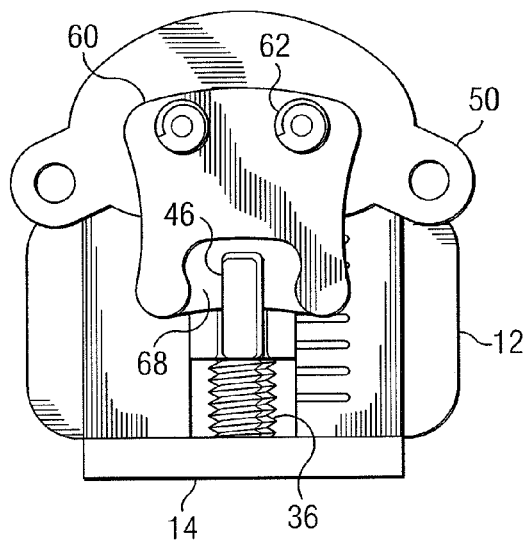
Figure 9:
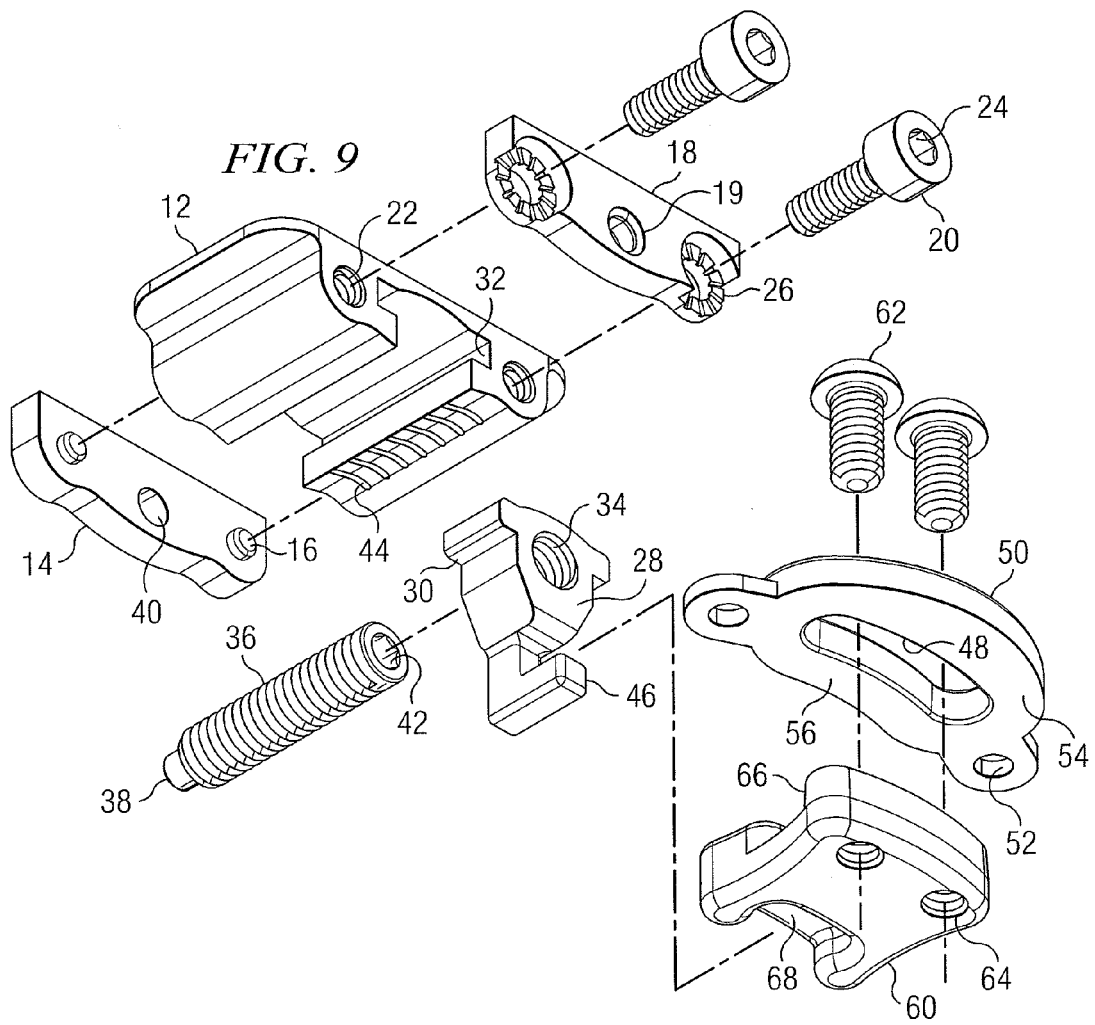
Figure 10:
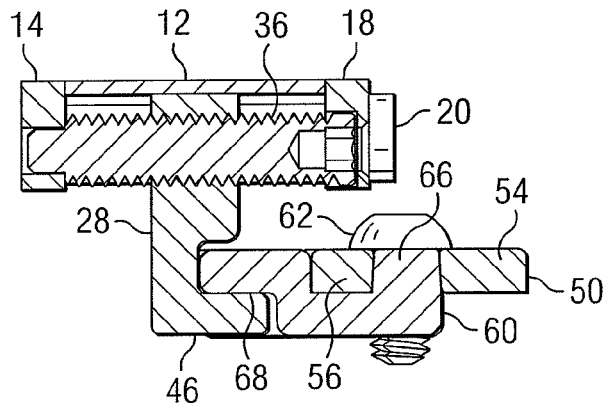

FIG. 1 illustrates an example oral appliance 100 for improving a user's breathing. In general, oral appliance 100 may be used to treat sleep disordered breathing, such as snoring or obstructive sleep apnea, through forward adjustment of the user's lower jaw relative to the upper jaw. This forward adjustment opens the breathing passage more fully and facilitates improved breathing through the user's nose and mouth. In certain embodiments, oral appliance 100 remains entirely within the user's mouth and surfaces of oral appliance 100 that may contact the interior of the user's mouth are smooth to prevent injury or discomfort.

Oral appliance 100 includes an upper arch 102 configured to receive at least some of a user's upper teeth, a lower arch 104 configured to receive at least some of the user's lower teeth, and an adjustment mechanism 10. Upper arch 102 and lower arch 104 may include molds of at least some of the user's upper and lower teeth, respectively, for improved performance and comfort. Adjustment mechanism 10 couples lower arch 104 to upper arch 102 and may be adjusted to pull lower arch 104 forward to facilitate improved breathing. In certain embodiments, adjustment mechanism 10 may also vertically position lower arch 104 relative to upper arch 102 to determine the opening of the user's lower jaw. The components of adjustment mechanism 10 may be made from any suitable material such as, for example, a biocompatible metal or hard plastic.

FIGS. 2A through 5B illustrate an example adjustment mechanism 10 for use with oral appliance 100. In certain embodiments, adjustment mechanism 10 may include body 12, hook 28, adjustor 36, and receiver 50. Body 12 may be integrated into or coupled to upper arch 102. Body 12 may include a rear plate 14, one or more rear fasteners 16, a front plate 18, and one or more front fasteners 20. In certain embodiments, body 12 may further include one or more fastener passages 22, one or more guides 32, and one or more adjustment indicators 44. Hook 28 may include flange 30, adjustor passage 34, and arm 46.

When assembled, rear plate 14 may be coupled to body 12 through the use of one or more fasteners 16. Fasteners 16 may be threaded fasteners, pins, or any other appropriate fastener to couple rear plate 14 to body 12. Hook 28 may be coupled to body 12 through the use of one or more flanges 30 engaged within the one or more guides 32. Adjustor 36 may include pin 38 and opening 42. Opening 42 may be square, hexagonal, or any other appropriate shape to allow for a rotational force to be applied to adjustor 36. Adjustor 36 may be positioned within adjustor passage 34 of hook 28 and pin 38 may be aligned with and inserted into hole 40 of rear plate 14. Front plate 18 may be coupled to body 12 through the use of one or more fasteners 20. Fasteners 20 may include threaded fasteners, pins, or any other appropriate fastener to couple front plate 18 to body 12. In certain embodiments, front plate 18 may include one or more structures to lock or secure one or more fasteners 20. For example, in embodiments utilizing a threaded fastener 20 as shown, front plate 18 may include one or more grooves and associated projections 26 to better secure fastener 20 in place.

In certain embodiments, front plate 18 may include an opening 19 that substantially aligns with opening 42 of adjustor 36. In operation, opening 19 may provide access to opening 42 of adjustor 36 for locational adjustment of hook 28. In certain embodiments, adjustor 36 may be threaded and may engage cooperative threads of adjustor passage 34 of hook 28 such that rotation of adjustor 36 moves hook 28 forward or rearward relative to body 12.

Receiver 50 is configured to receive arm 46 of hook 28 such that forward adjustment of hook 28 pulls lower arch 104 forward. Receiver 50 may be fully integrated into, permanently coupled to, or separate and removable from lower arch 104. In certain embodiments, receiver 50 may include one or more openings 52 that may be used to couple receiver 50 to lower arch 104 through the use of any appropriate fastener. In certain embodiments, receiver 50 may also include slot 48 separating front shelf 54 from rear shelf 56. In operation, hook 28 may engage either front shelf 54 or rear shelf 56. In certain embodiments, the use of rear shelf 56 may provide additional extension of lower arch 104 in the forward direction relative to the use of front shelf 54.

Receiver 50 may be modified according to particular needs to provide increased flexibility. For example, the vertical location of front shelf 54 and/or rear shelf 56 relative to lower arch 104 may be adjusted or otherwise modified, either during or after initial construction of receiver 50. As another example, receivers 50 with varying vertical dimensions may be provided, such that the use of a particular receiver 50 may be selected to define a prescribed vertical separation between upper arch 102 and lower arch 104 and thus a prescribed opening of the user's lower jaw. As another example, the vertical location of front shelf 54 and/or rear shelf 56 may be selected by coupling receiver 50 to lower arch 104 in either of two possible orientations (i.e., with a particular horizontal surface facing up or facing down). As another example, receivers 50 with varying horizontal dimensions may be provided, such that the use of a particular receiver 50 may be selected to define a prescribed forward location (or range of locations) for lower arch 104 relative to upper arch 102.

Slot 48 may allow horizontal movement of lower arch 104 relative to lower upper 102 when lower arch 104 is coupled to upper arch 102. Similarly, the posterior surface of front shelf 54 and/or rear shelf 56 may be shaped to guide the horizontal movement of lower arch 104 relative to upper arch 102 in an arc-shaped or other desirable path.

FIGS. 6A through 6C illustrate example hooks 28 with varying lengths, for use with adjustment mechanism 10. In operation, the use of a particular hook 28 may be selected to define a prescribed vertical separation between upper arch 102 and lower arch 104 and thus a prescribed opening of the user's lower jaw. For example, in the embodiments shown, the use of hook 28c may allow for greater vertical separation between upper arch 102 and lower arch 104 than the vertical separation allowed with the use of hooks 28a or 28b. In particular embodiments, the use of hooks 28 with varying lengths, together with the use of receivers 50 with varying vertical dimensions, may provide an increased range and/or precision for selection of a prescribed opening of the user's lower jaw.

FIGS. 7A through 7C illustrate example receivers with varying dimensions, for use with adjustment mechanism 10. In operation, the use of a particular receiver may be selected to define a prescribed forward location (or range of forward locations) for lower arch 104 relative to upper arch 102 and thus a prescribed forward location (or range of forward locations) for the user's lower jaw. For example, in the embodiments shown, the use of receiver 50c may allow for lower arch 104 to be positioned further forward with respect to upper arch 102 than with the use of receivers 50a or 50b. In particular embodiments, the use of receivers 50 with varying dimensions may provide an increased range and/or precision for adjusting the forward location of lower arch 104 relative to upper arch 102.

FIGS. 8A through 10 illustrate an example adjustment mechanism 10 utilizing an example extender 60. In certain embodiments, extender 60 couples to receiver 50 and operates to receive arm 46 of hook 28 such that the forward positioning of lower arch 104 is greater than that provided without extender 60.

Figure 11A:
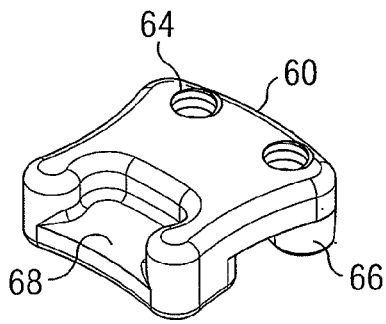
FIGS. 11A and 11B illustrate an example extender.
Figure 11B:
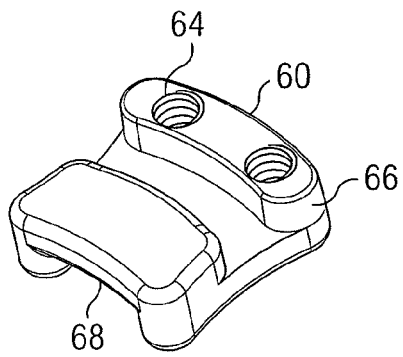

FIGS. 11A and 11B illustrate an example extender 60 for use with an example adjustment mechanism 10. In certain embodiments, extender 60 may include a shelf 68 that engages arm 46 of hook 28. In certain embodiments, extender 60 may also include one or more projections 66 that may cooperatively engage slot 48 of receiver 50. In certain embodiments, extender 60 may also include one or more openings 64 that may cooperate with one or more fasteners 62 to couple extender 60 to receiver 50, such as via slot 48. Fastener 62 may be a threaded fastener, pin, or any other appropriate fastener for coupling extender 60 to receiver 50.

Figure 12A:
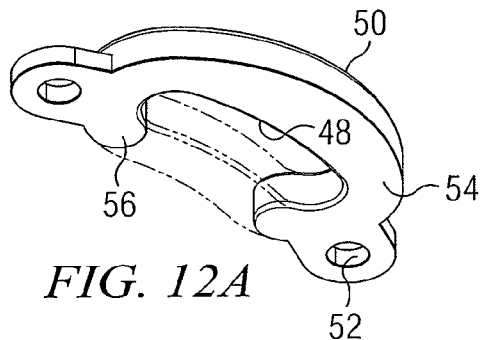
FIGS. 12A and 12B illustrate example receivers.
Figure 12B:
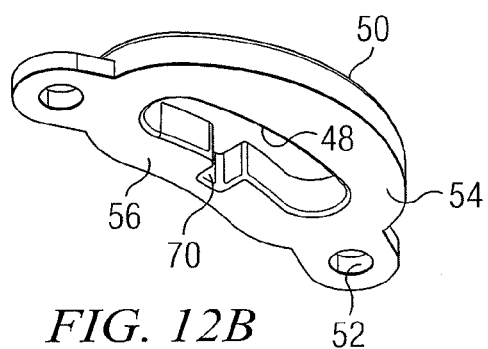

FIGS. 12A and 12B illustrate example receivers 50 for use with example adjustment mechanisms 10. As shown in FIG. 12A, in certain embodiments, receiver 50 may include only a single shelf 54, in which case slot 48 may be fully or partially exposed in the rearward direction. As shown in FIG. 12B, receiver 50 may include notch 70 in slot 48. In operation, the use of receiver 50 including only a single shelf 54 or including notch 70 may allow hook 28 to engage or disengage from shelf 54 of receiver 50 after oral appliance 100 has been inserted into a user's mouth.

Figure 13:
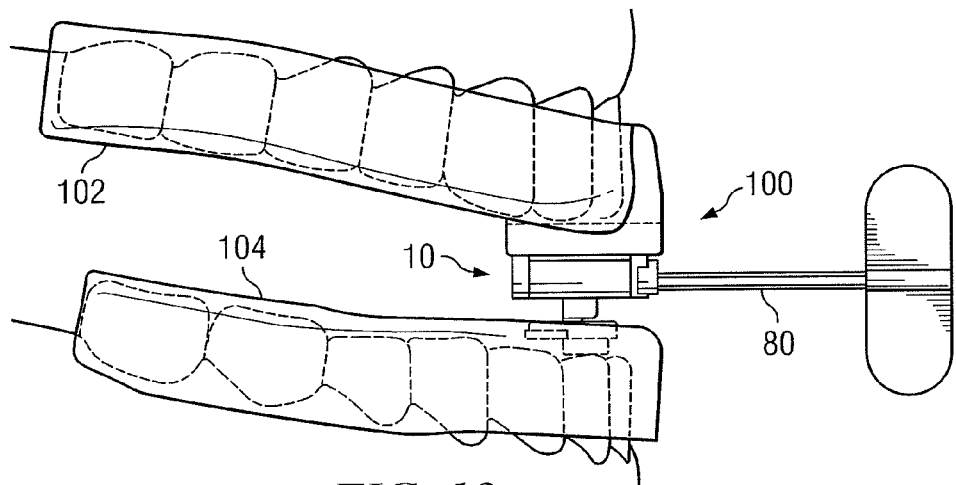
FIGS. 13 through 16 illustrate an example adjustment mechanism utilizing an example adjustment key.

FIG. 13 illustrates an example oral appliance 100 with an example adjustment key 80. Adjustment key 80 may have a cross-section that is hexagonal, square, or any other appropriate shape. In certain embodiments, adjustment key 80 may be used to exert a rotational force on adjustor 36 causing adjustor 36 to turn and thereby provide adjustment of hook 28, forward or rearward.

Figure 15:
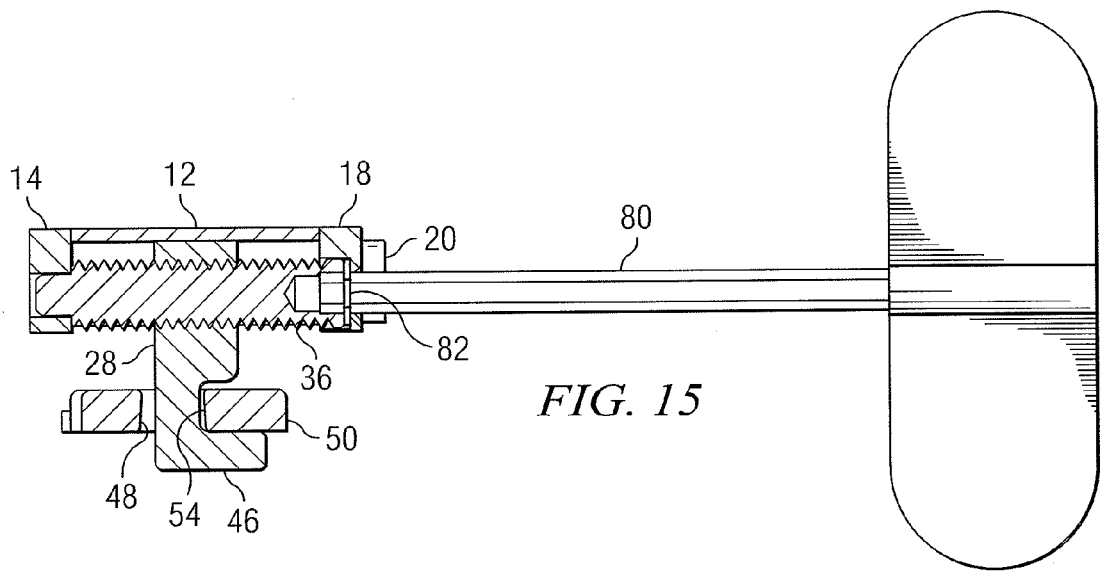
Figure 14:
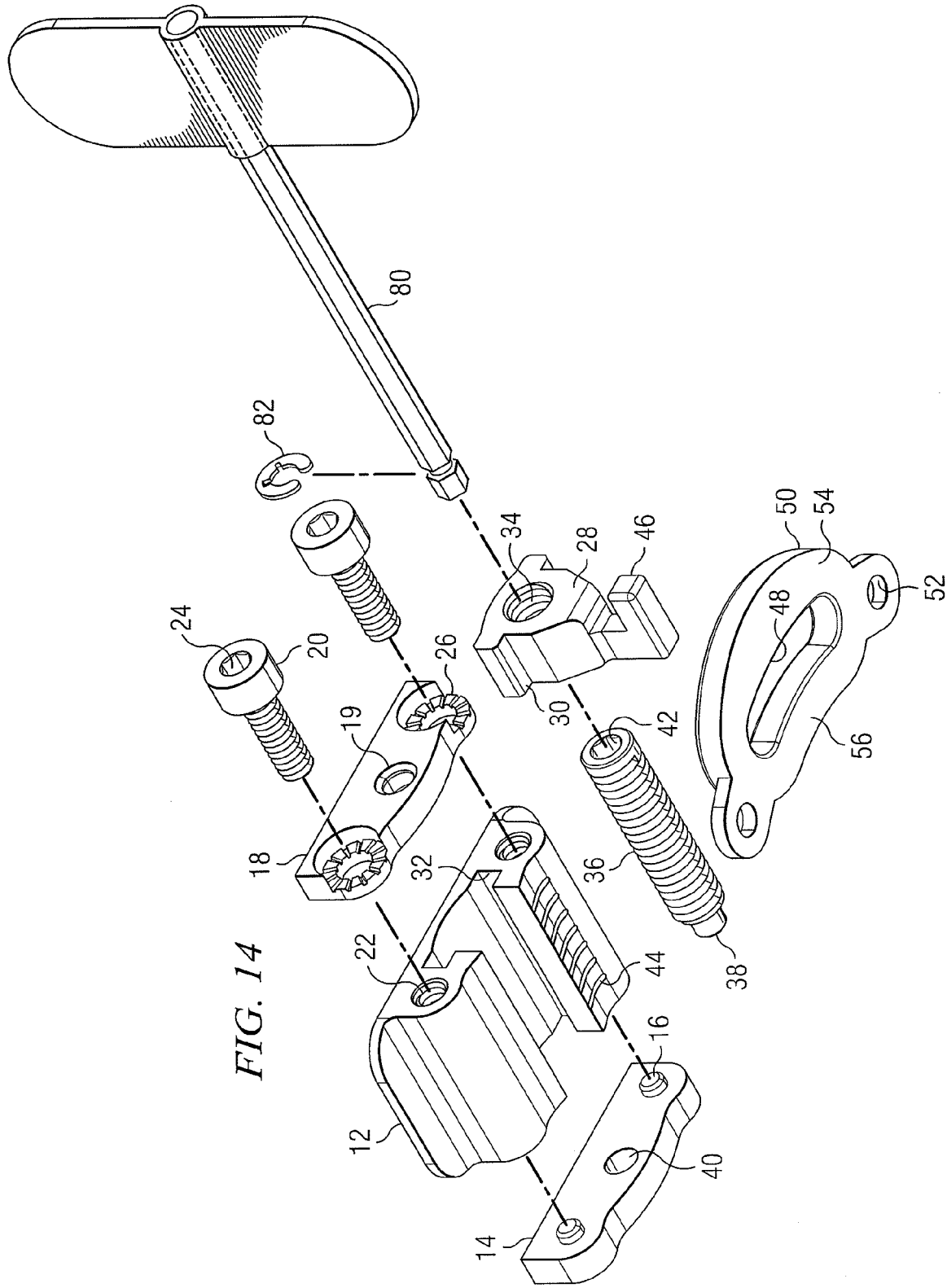
Figure 16:
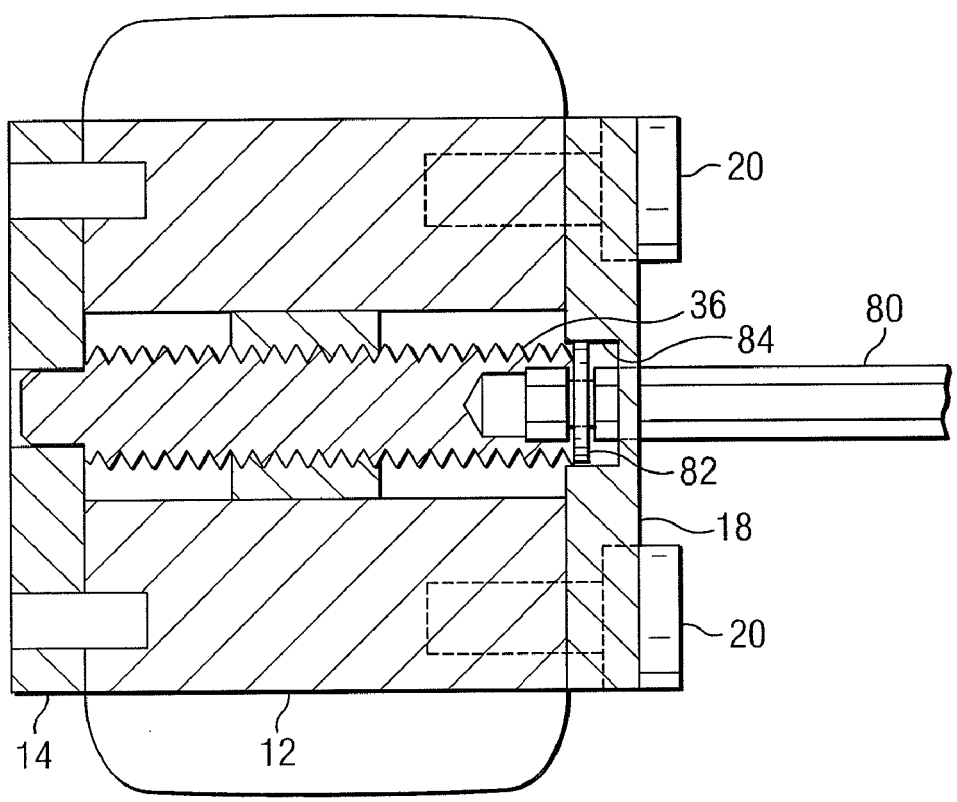
Figure 17:
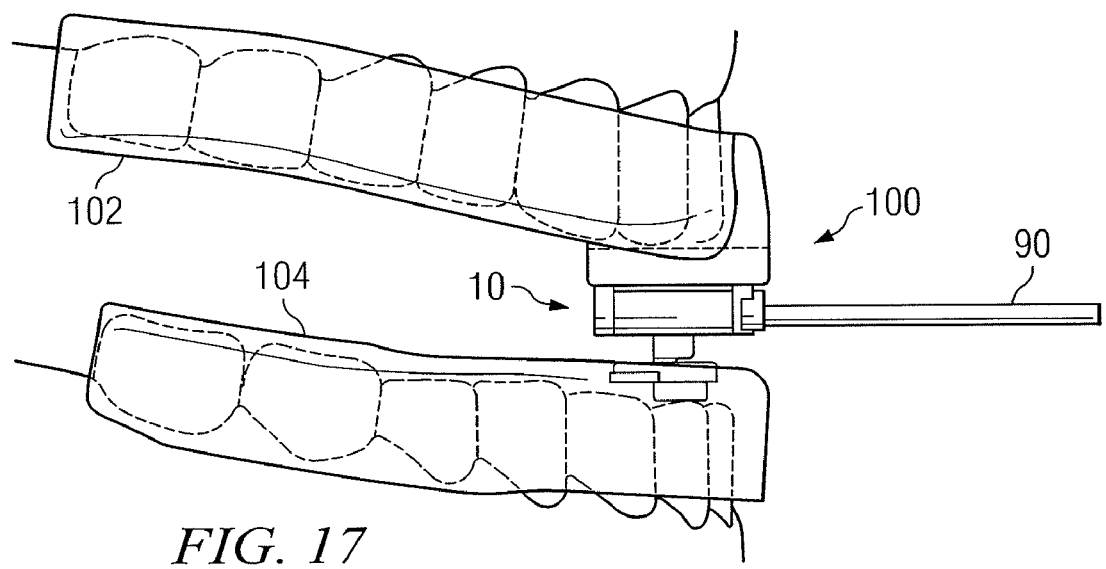
FIGS. 17 through 19B illustrate an example adjustment mechanism utilizing an example extension post.
Figure 18:
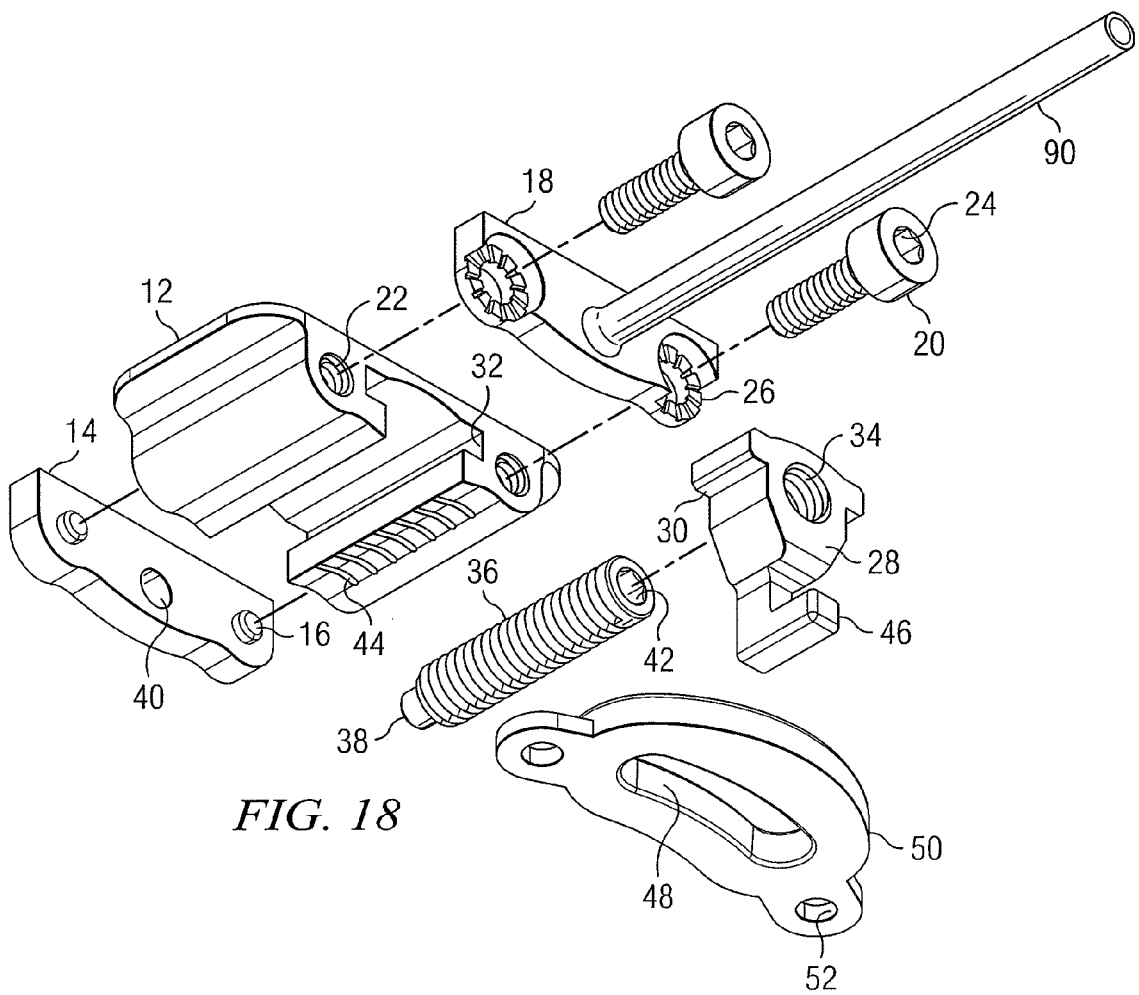

FIGS. 14 through 16 illustrate example adjustment mechanisms 10 utilizing example adjustment keys 80. In certain embodiments, adjustment key 80 may be coupled to adjustment mechanism 10 through the use of retainer ring 82 and notch 84. In operation, retainer ring 82 may engage notch 84, thus preventing removal of adjustment key 80. In operation, embodiments of adjustment mechanism 10 including adjustment key 80 and retaining ring 82 may be used by a particular user during a trial period for oral appliance 100. During this trial period, the user and/or a clinician may make periodic adjustments to adjustment mechanism 10 through the use of adjustment key 80 to achieve the desired positioning of lower arch 104 relative to upper arch 102. In these embodiments, once the desired positioning has been achieved, adjustment key 80 and retaining ring 82 may be removed. In these embodiments, once the desired positioning has been achieved, front plate 18 may be replaced with a front plate 18 that does not include an opening 19.

FIGS. 17 through 19B illustrate an example oral appliance 100 with an example extension post 90. Extension post 90 may be formed of any suitable material, such as a metal or hard plastic. In certain embodiments, extension post 90 may be used to couple oral appliance 100 to one or more other devices and/or to orient one or more other devices relative to oral appliance 100. For example, extension post 90 may be used to couple oral appliance 100 to a breathing device, such as a venting seal, a face mask, or a nose mask. In a particular embodiment, extension post may be used to couple oral appliance 100 to a mask associated with a continuous positive airway pressure (CPAP) system.

In certain embodiments, extension post 90 may be substantially rigid, to provide for sufficiently precise positioning of one or more devices relative to upper arch 102. For example, in certain embodiments, extension post 90 may be used to provide substantially precise and repeatable positioning of a face mask or nose mask relative to upper arch 102. The length of extension post 90 may vary depending upon its intended use. For example, extension post 90 may be substantially shorter if it is intended to be used to couple a venting seal to oral appliance 100 than if it is intended to couple a nose mask to oral appliance 100. The invention contemplates any reasonable length of extension post 90, so long as the length is appropriate to perform the intended function.

Figure 19A:
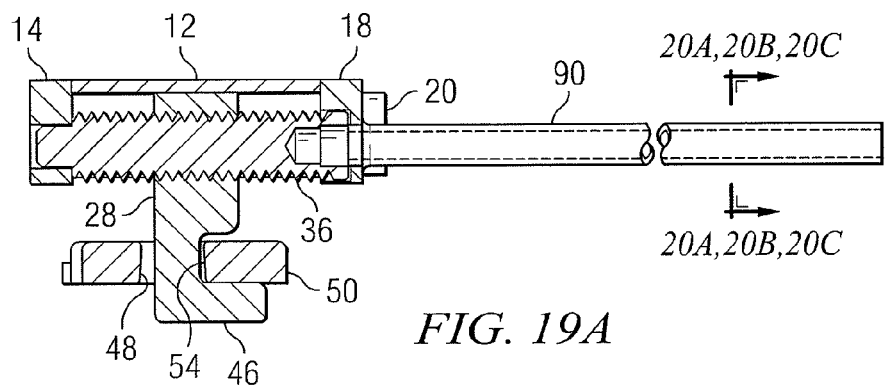
Figure 19B:
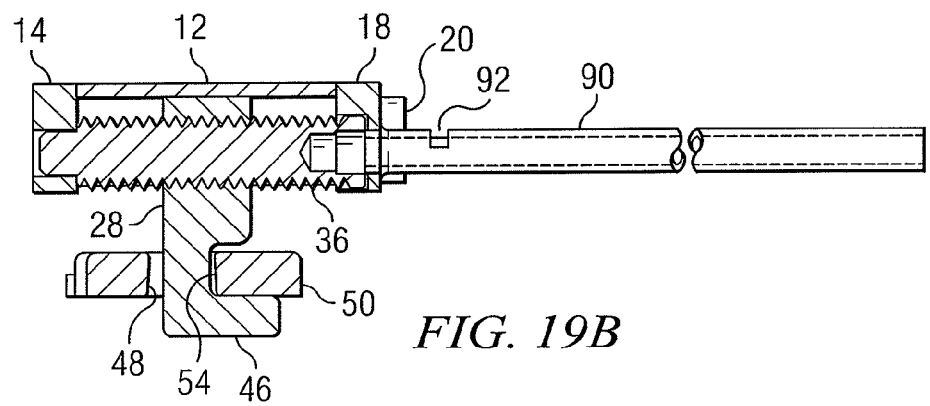

In certain embodiments, extension post 90 may include one or more features that can operate to index or assist in securing one or more devices to extension post 90. For example, as shown in FIG. 19B, extension post 90 may include one or more locators 92 at one or more positions along the length of extension post 90. In operation, a device coupled to or guided by extension post 90 may include one or more structures that can cooperate with the one or more locators 92 to index or assist in securing the device. In the embodiment shown, locator 92 is in the form of a notch, however, in alternative embodiments, locator 92 may be in the form of a ridge, protrusion, or any other appropriate shape or structure. In particular embodiments, the position of locator 92 may be adjustable.

In certain embodiments, extension post 90 may be coupled to front plate 18. In these embodiments, extension post 90 may be coupled through the use of any appropriate means, such as welding or threaded coupling. In alternative embodiments, extension post 90 may be integrally formed with front plate 18. In certain embodiments, extension post 90 may be substantially hollow and may couple to front plate 18 such that the hollow interior of extension post 90 substantially aligns with an opening 19. In operation, hollow portion 92 may provide access to adjustor 36 through opening 19. The cross-sectional shape of extension post 90 may take any appropriate form, so long as it remains reasonable for the intended function.

Figure 20A:
FIGS. 20A through 20C illustrate transverse cross-sectional views of example extension posts.
Figure 20B:
Figure 20C:

FIGS. 20A through 20C illustrate transverse cross-sectional views of example extension posts 90. As shown, extension post 90 may have a cross sectional shape that is a circle, oval, or diamond. In certain embodiments, non-circular cross-sections may function to more precisely position a device coupled to oral-appliance 100 through the use of extension post 90, by substantially limiting the likelihood that the device will rotate about the extension post 90.

In certain embodiments, receiver 50 may be removable. For example, lower arch 104 may include a recess that allows receiver 50 to be positioned within, and then removed from, lower arch 104. In embodiments including a removable receiver 50 and a recess in lower arch 104, the recess may be integrally formed in lower arch 104. In alternative embodiments, the recess may be formed in or by a housing that is included in lower arch 104.

Figure 21:
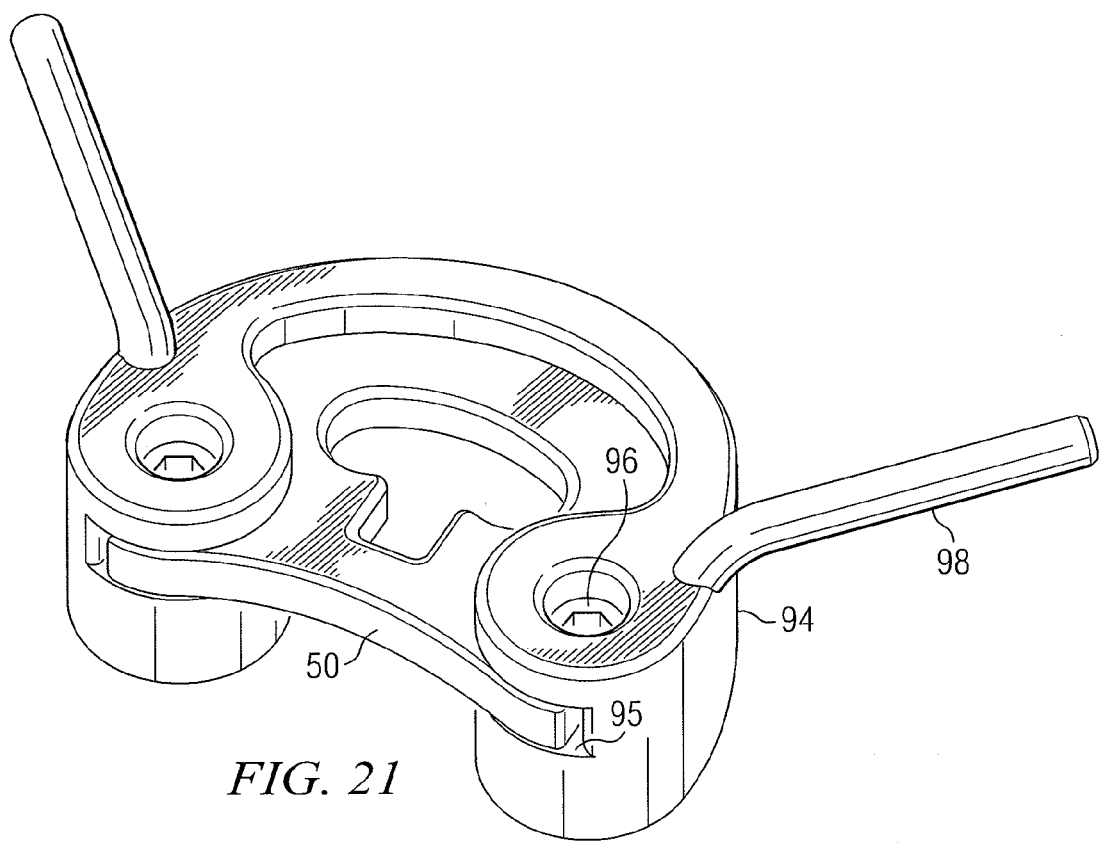
FIGS. 21 through 23 illustrate an example housing, for use with an example adjustment mechanism.
Figure 22:
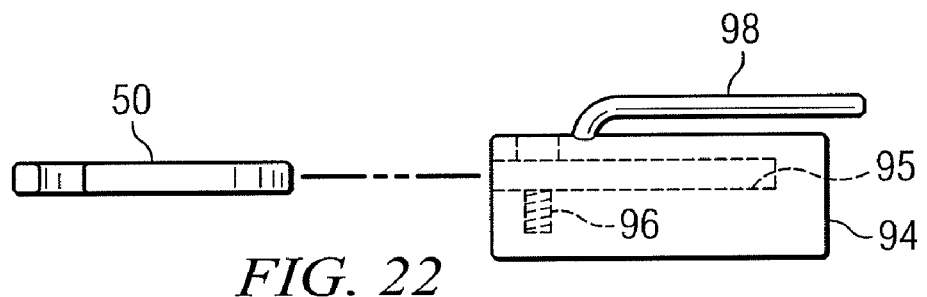
Figure 23:
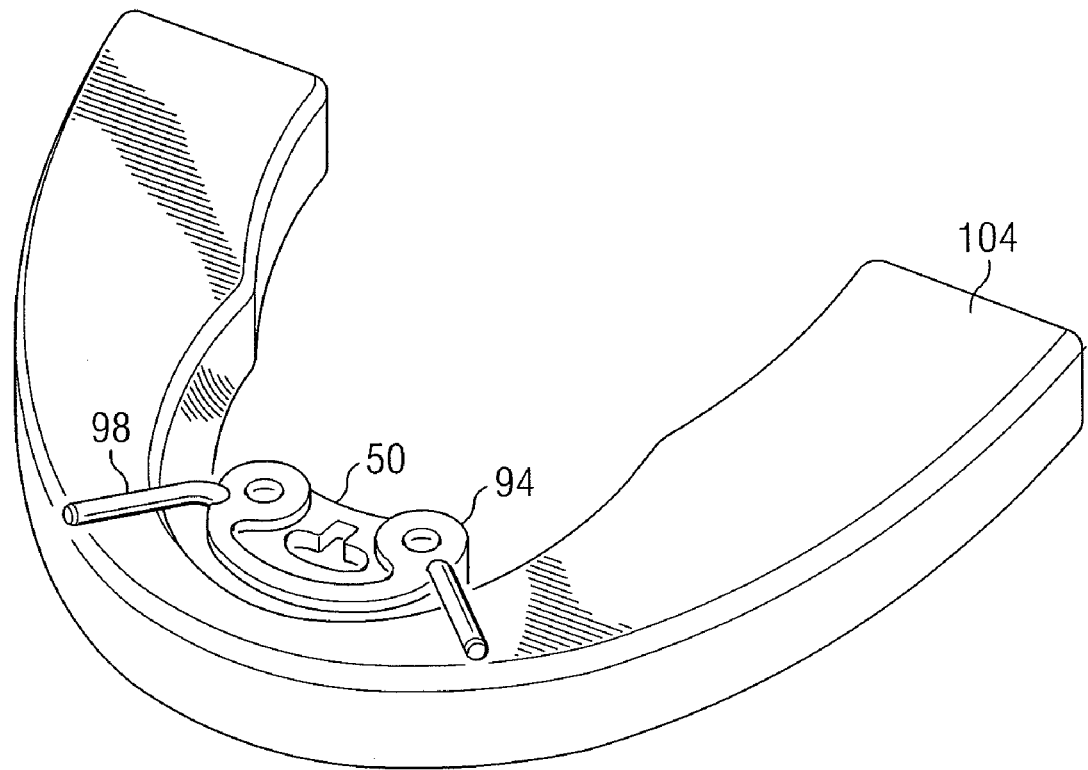

FIGS. 21 through 23 illustrate an example housing 94, for use with an example adjustment mechanism 10. In certain embodiments, adjustment mechanism 10 may include housing 94 to position and secure receiver 50. Housing 94 may be made of any appropriate material, such as metal or hard plastic. In certain embodiments, housing 94 may be integrally formed with lower arch 104. As shown, housing 94 may define recess 95 to accept receiver 50 within housing 94. In certain embodiments, housing 94 may include one or more fasteners 96 to secure receiver 50 within recess 95. In a particular embodiment, fastener 96 may be a threaded set-screw.

In certain embodiments, housing 94 may include one or more projections 98 that may be used to orient and/or secure housing 94 to lower arch 104. In particular embodiments, as in the example shown in FIG. 23, one or more projections 98 may be used to orient housing 94 to lower arch 104. In these embodiments, once housing 94 is properly oriented, housing 94 may be luted to (or otherwise secured to) lower arch 104. In certain embodiments, some or all of projections 98 may be removed before or after housing 94 is completely secured to lower arch 104.

FIGS. 24A through 25C illustrate example receivers 50, for use with an example housing 94. As shown, receiver 50 may have varying dimensions and the location of certain features of receiver 50 may vary. In operation, the use of a particular receiver 50 may be selected to define a prescribed forward location (or range of locations) for lower arch 104 relative to upper arch 102. For example, in the embodiments shown, the use of receiver 50f may allow for lower arch 104 to be positioned further forward with respect to upper arch 102 than with the use of receivers 50d and 50e. In particular embodiments, the use of receivers 50 with varying dimensions may provide an increased range and/or precision for adjusting the forward location of lower arch 104 relative to upper arch 102.

Figure 24A:
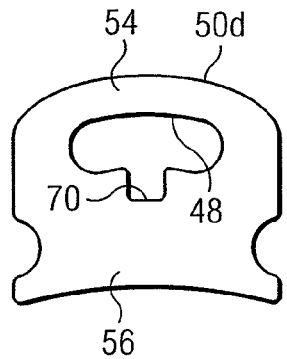
FIGS. 24A through 25C illustrate example receivers, for use with an example housing.
Figure 24B:
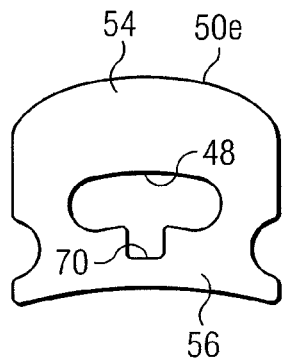
Figure 24C:
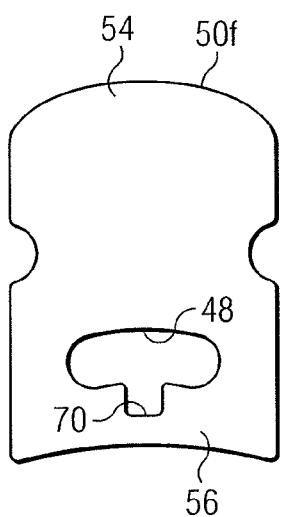
Figure 24D:
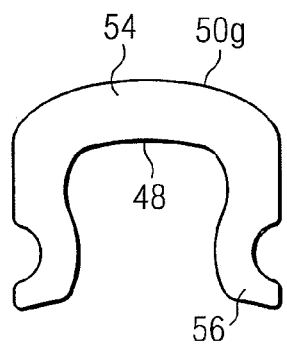

As shown in FIG. 24D, in certain embodiments, receiver 50 may include only a single shelf 54, in which case slot 48 may be fully or partially exposed in the rearward direction. In operation, the use of receiver 50 including only a single shelf 54 (or including notch 70) may allow hook 28 to engage or disengage from shelf 54 of receiver 50 after oral appliance 100 has been inserted into a user's mouth.

Figure 25A:
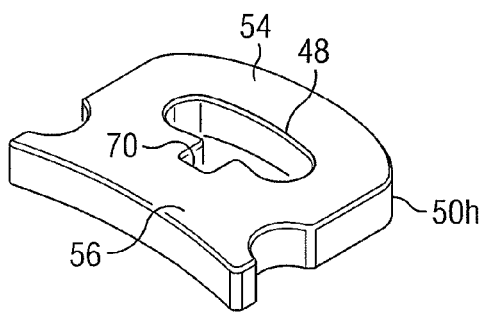
Figure 25B:
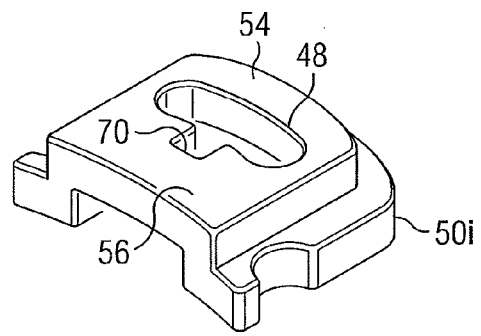
Figure 25C:
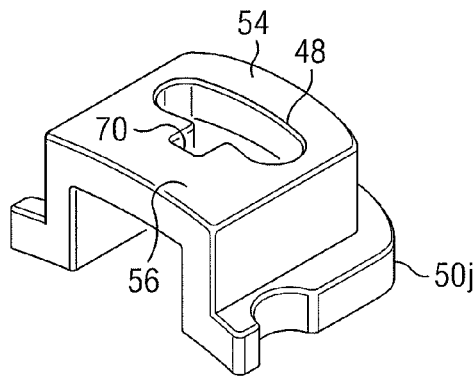

As shown in FIGS. 25A through 25C, receiver may have varying vertical dimensions. In operation, the use of a particular receiver 50 may be selected to define a prescribed vertical separation between upper arch 102 and lower arch 104 and thus a prescribed opening of the user's lower jaw. For example, in the embodiments shown, the use of receiver 50*j* may allow for greater vertical separation between upper arch 102 and lower arch 104 than the vertical separation allowed with the use of receivers 50*h* and 50*i*. In particular embodiments, the use of receivers 50 with varying vertical dimensions may provide an increased range and/or precision for selection of a prescribed opening of the user's lower jaw.

Figure 26:
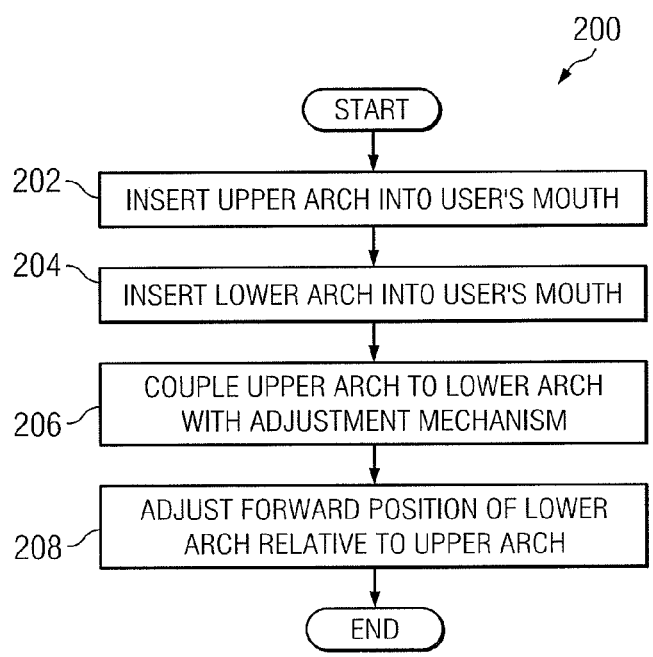
FIG. 26 illustrates an example method of improving a user's breathing.

FIG. 26 illustrates an example method of improving a user's breathing, indicated generally at 200. At step 202, upper arch 102 is inserted into the user's mouth. At step 204, lower arch is inserted into the user's mouth. At step 206, upper arch 102 is coupled to lower arch 104 by adjustment mechanism 10. In certain embodiments, adjustment mechanism 10 includes a body 12 coupled to upper arch 102, an adjustor 36, a hook 28, and a receiver 50 coupled to lower arch 104. In certain embodiments, upper arch 102 is coupled to lower arch 104 by engaging shelf 54 of receiver 50 with arm 46 of hook 28. In particular embodiments, the initial forward position of lower arch 104 relative to upper arch 102 is determined by engaging a particular one of multiple shelves 54 of receiver 50. In alternative embodiments, the initial forward position of lower arch 104 relative to upper arch 102 is determined by engaging shelf 68 of extender 60 coupled to receiver 50. At step 208, the forward position of lower arch 104 relative to upper arch 102 is adjusted to facilitate improved breathing by the user. In certain embodiments, the forward position is adjusted by rotating adjustor 36 using adjustment key 80 or in any other appropriate manner.

FIGS. 27 through 30 illustrate an example oral appliance 500 for improving a user's breathing according to an alternative embodiment. In general, oral appliance 500 may be used to treat sleep disordered breathing, such as snoring or obstructive sleep apnea, through forward adjustment of the user's lower jaw relative to the upper jaw. This forward adjustment opens the breathing passage more fully and facilitates improved breathing through the user's nose and mouth. In certain embodiments, oral appliance 500 remains entirely within the user's mouth and surfaces of oral appliance 500 that may contact the interior of the user's mouth are smooth to prevent injury or discomfort. In certain embodiments, oral appliance 500 may be substantially similar in function to oral appliance 100 of FIG. 1, though oral appliance 500 may be substantially different in structure from oral appliance 100.

Figure 27:
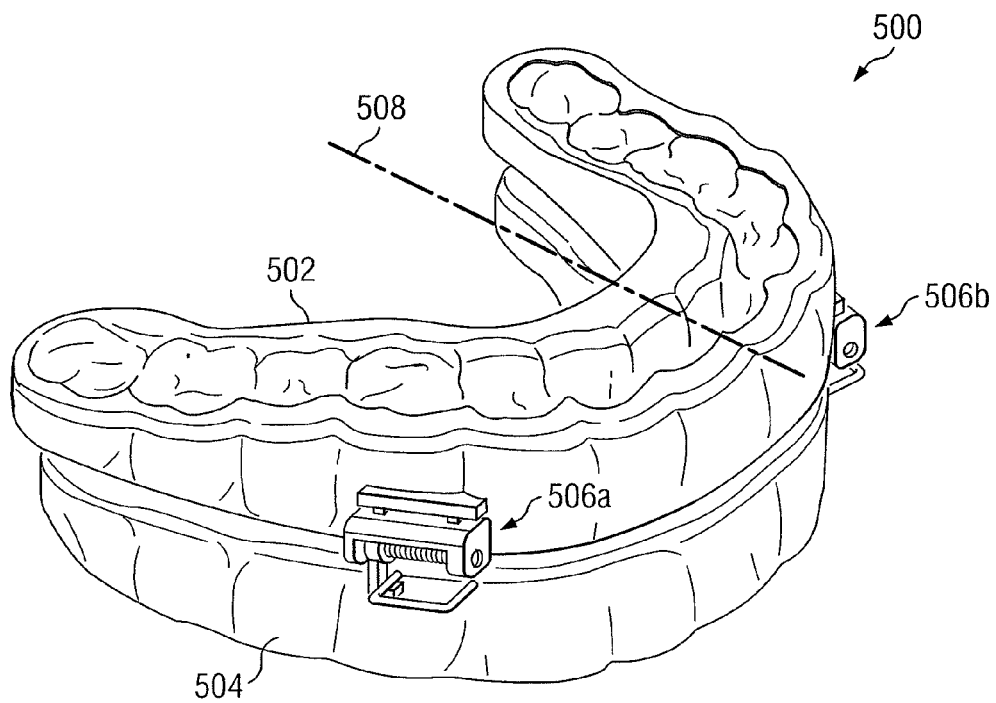
FIGS. 27 through 30 illustrate various views of an example oral appliance for improving a user's breathing according to an alternative embodiment.
Figure 28:
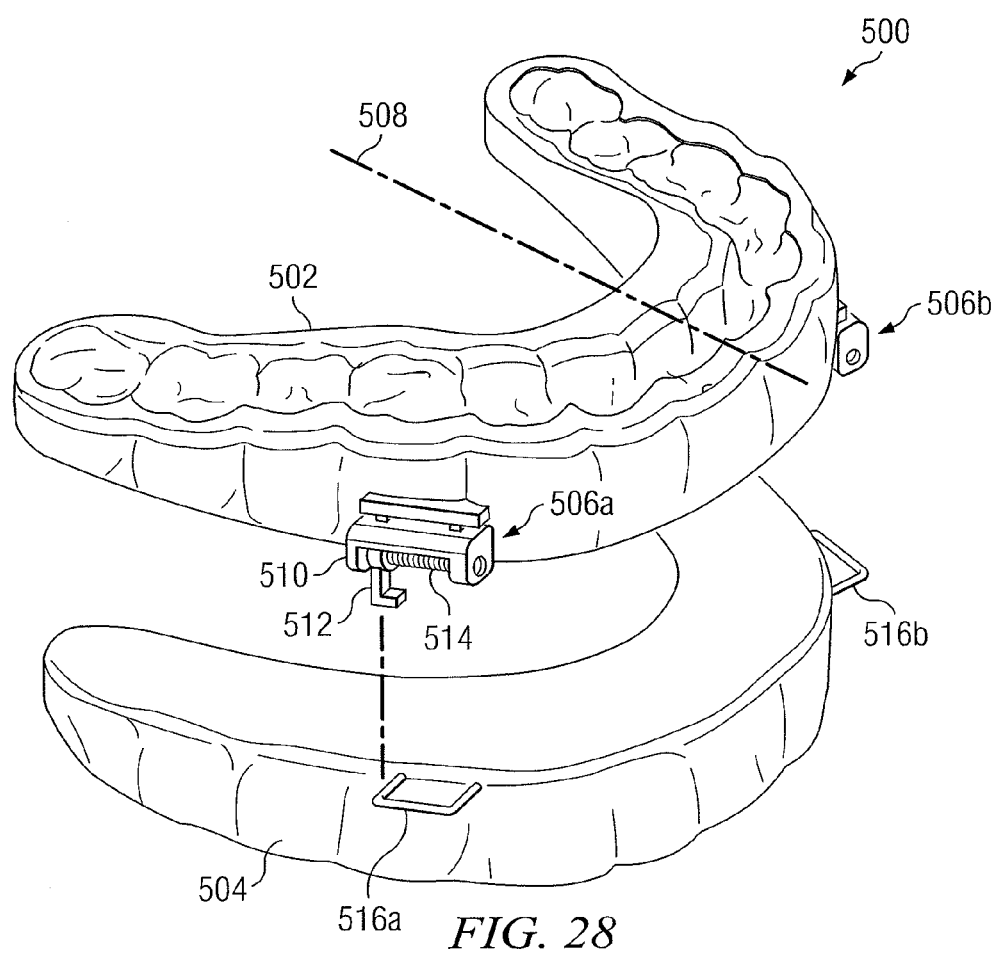

FIGS. 27 and 28 illustrate a perspective view and an exploded view, respectively, of oral appliance 500. Oral appliance 500 includes an upper arch 502 configured to receive at least some of a user's upper teeth, a lower arch 504 configured to receive at least some of the user's lower teeth, and multiple adjustment mechanisms 506*a* and 506*b*. Upper arch 502 and lower arch 504 may include molds of at least some of the user's upper and lower teeth, respectively, for improved performance and comfort. In certain embodiments, upper and lower arches 502 and 504 may be substantially similar in structure and/or function to upper and lower arches 102 and 104, respectively, of FIG. 1.

In the illustrated example, adjustment mechanisms 506*a* and 506*b* are each located approximately equal distances from the plane 508 bisecting left and right halves of the upper and lower arches 502 and 504. The position of plane 508 relative to upper and lower arches 502 and 504 substantially aligns with the mesial plane of the user's body when lower and upper arches 502 and 504 are coupled to the user's teeth. Although oral appliance 500 shows two adjustment mechanisms 506*a* and 506*b* positioned symmetrically about plane 508 with respect to each other, alternative embodiments may position one adjustment mechanism 506*a* or 506*b* closer to the mesial plane than the other adjustment mechanism. In certain embodiments, adjustment mechanisms 506*a* and/or 506*b* may be positioned proximate to the user's molars. In alternative embodiments, adjustment mechanisms 506*a* and/or 506*b* may be positioned proximate to the user's bicuspids. The components of adjustment mechanisms 506*a* and 506*b* may be made from any suitable material such as, for example, a biocompatible metal or hard plastic.

Adjustment mechanisms 506*a* and 506*b* may each couple lower arch 504 to upper arch 502 and may each be individually adjusted to move lower arch 504 relative to upper arch 502. For example, adjustment mechanism 506*a* and/or 506*b* may be used to pull lower arch 504 forward to facilitate improved breathing. In certain embodiments, adjustment mechanisms 506*a* and/or 506*b* may also vertically position lower arch 504 relative to upper arch 502 to determine the opening of the user's lower jaw. In certain embodiments, adjustment mechanisms 506*a* and 506*b* may be configured to engage each other in a manner that repositions lower arch 504 in a forward direction relative to upper arch 502 and in a manner that prevents sagittal separation of the upper and lower arches 502 and 504 beyond a fixed distance defined at least in part by adjustment mechanisms 506*a* and 506*b*. In the context of the human body, sagittal movement of the jaw refers to the opening and closing of the jaw.

Adjustment mechanisms 506*a* and 506*b* may each include a body 510, hook 512, adjuster 514, and receiver 516. In certain embodiments, adjustment mechanisms 506, body 510, hook 512, adjuster 514, and/or receiver 516 may be substantially similar in structure and/or function to certain embodiments of adjustment mechanism 10, body 12, hook 28, adjustor 36, and receiver 50, respectively. In particular embodiments, body 510, hook 512, adjuster 514, and/or receiver 516 may be substantially similar in function to certain embodiments of adjustment mechanism 10, body 12, hook 28, adjustor 36, and receiver 50, respectively, though adjustment mechanisms 506, body 510, hook 512, adjuster 514, and/or receiver 516 be substantially different in structure to certain embodiments of adjustment mechanism 10, body 12, hook 28, adjustor 36, and receiver 50, respectively. Adjustment mechanism 10, body 12, hook 28, adjustor 36, and receiver 50 are discussed previously with reference to FIGS. 2A through 5B. Hooks 512 may have various lengths, as discussed previously with reference to FIGS. 6A through 6C. In certain embodiments, the hook 512 of adjustment mechanism 506*a* may differ in length from the hook of adjustment mechanism 506*b*.

Figure 29:
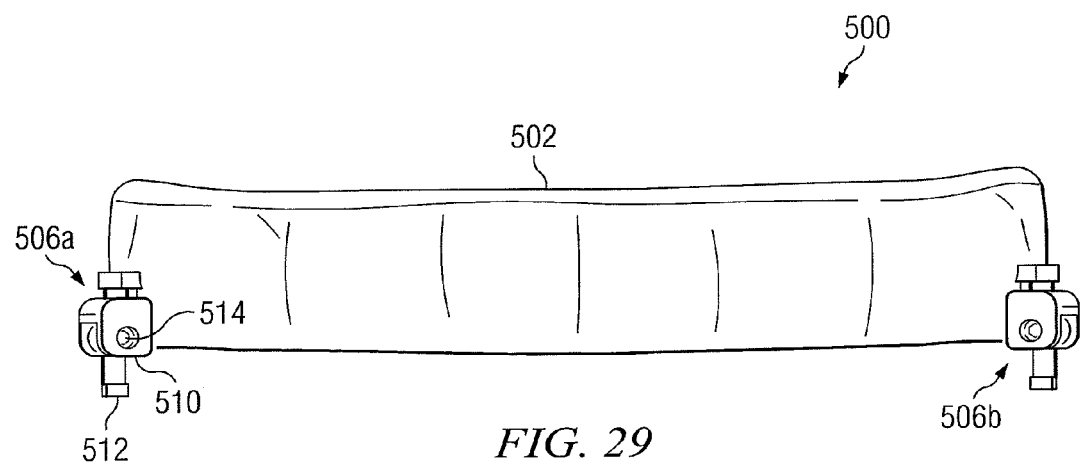

In certain embodiments, body 510 may be fully integrated into, permanently coupled to, or separate and removable from upper arch 502. As shown in FIGS. 27 through 29, for example, body 510 may be coupled to upper arch 502 by epoxy or other suitable fastener. In an alternative embodiment, upper arch 502 may include receptors configured to removably snap bodies 510 into place. In still another embodiment, upper arch 502 may be formed around at least a portion of bodies 510.

Figure 30:
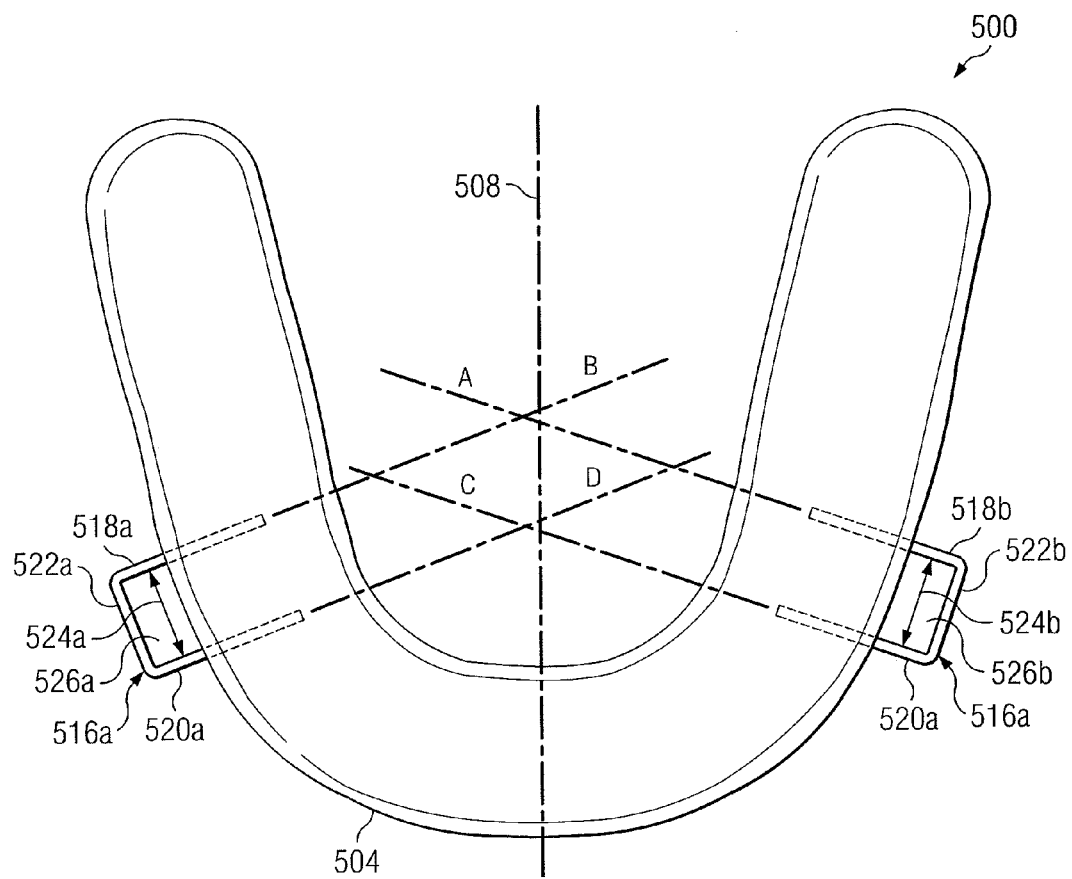

In various embodiments, receivers 516 may be fully integrated into, permanently coupled to, or separate and removable from lower arch 504. As shown in FIG. 30, for example, lower arch 504 may be formed around at least a portion of each receiver 516. As another example, receivers 516 may be permanently coupled to lower arch 104 by epoxy or other suitable fastener. In still another embodiment, lower arch 504 may include receptors configured to removably snap receivers 516 into place.

As shown in FIGS. 27 through 30, bodies 510 are coupled to upper arch 502 and receivers are coupled to lower arch 504. In an alternative embodiment, body 510 and receiver 516 may be inverted with respect to each other, such that body 510 may be integrated into or coupled to lower arch 504 and receiver 516 may be integrated into or coupled to upper arch 502. In still another embodiment, adjustment mechanisms 506a and 506b may be inverted with respect to each other such that receiver 516a and body 510b are both coupled to upper arch 502 and receiver 516b and body 510a are both coupled to lower arch 504 (or vice versa). Inverting the adjustment mechanisms 506 with respect to each other in this manner may enable adjustment options that differ from those options provided by alternative embodiments.

As shown in FIG. 30, each receiver 516 may include a back rail 518 and a front rail 520 coupled to each other by a brace 522. In certain embodiments, rails 518 and 520 are substantially parallel to each other and spaced apart from each other by a maximum distance 524. Each rail 518 and 520 may be coupled to lower arch 104 at respective ends such that rails 518 and 520 and cross brace 522 collectively define at least a portion of a slot 526. The slot 520 of each receiver is disposed on the labial side of lower arch 504 opposite from an interior area spanned and partially enclosed by the lingual side of lower arch 504. Although each receiver 516 in this example includes two rails 518 and 520 and one cross brace 522, any suitable number of rails 518 and 520 and/or cross braces 522 may be used. Although slots 526 are rectangular in shape in this example, slot 526 may have any suitable shape depending upon the shapes and positioning of cross braces 522 relative to the shapes and positioning of rails 518 and 520. For example, slots 526 may be trapezoidal in shape if rails 518 and 520 are not substantially parallel to each other.

In particular embodiments, receivers 516a and 516b may each be located approximately equal distances from the plane 508 bisecting left and right halves of the lower arch 504. Rails 518a, 518b 520a, and 520b may be coupled to lower arch 504 such that rails 518a, 518b, 520a, and 520b are substantially normal to the outer surface of lower arch 504 at the points where rails 518a, 518b, 520a, and 520b contact the outer surface. In certain embodiments, rails 518a, 518b 520a, and 520b may be coupled to lower arch 504 such that rails 518a, 518b, 520a, and 520b lie substantially along and/or are parallel to axis A, B, C, and D, respectively. In particular embodiments, axis A and B may intersect plane 508 at approximately the same point as each other and/or axis C and D may intersect plane 508 at approximately the same point as each other.

Receivers 516a and/or 516b may be configured to receive an arm of a respective hook 512 such that forward adjustment of the hook 412 pulls lower arch 504 forward. In certain embodiments, receivers 516a and/or 516b may be configured such that either rail 518 and/or 520 may engage hook 512. Receivers 516 may be modified according to particular needs to provide increased flexibility. For example, the vertical location of rails 518 and/or 520 relative to lower arch 104 may be adjusted or otherwise modified, either during or after initial construction of receivers 516.

Receivers 516 may be formed from any suitable material using a variety of manufacturing processes. In a particular embodiment, rails 120 and cross bars 130 are each nickel-free, stainless steel wires having a maximum cross-sectional width that is greater than approximately 0.040 inches and less than approximately 0.100 inches; however any suitable materials and/or dimensions may be used. In certain embodiment, rails 518 and 520 and cross bar 522 may be integrally formed from a single metallic piece. The integrally formed piece may be a single metallic piece bent to form rails 518 and 520 and cross bar 522. As another example, all or a portion of receiver 516 may be formed from an injection mold of nickel-free, stainless steel. In an alternative embodiment, receivers 516 may be formed by welding metallic pieces together. For example, rails 518 and 520 and/or cross bar 522 may each be metallic pieces that are welded together at areas where they contact each other. These contact areas may each be disposed along any suitable surface of rails 518 and 520 and/or cross bar 522. In still other embodiments, receivers 516 may be non-metallic. For example, receivers 516 may be integrally formed with lower arch 512 from the same material used to form lower arch 504.

Thus, particular embodiments may provide two adjustment mechanisms 506 that may be independently adjusted as desired to effect a variety of different positions of upper arch 502 relative to lower arch 504. In certain embodiments, adjustment mechanisms 506 may have forward-facing adjusters 514 that enable intra-oral adjustments while the oral appliance 500 is positioned in the user's mouth.

Although an example method is described, the steps may be accomplished in any appropriate order. For example, inserting the upper and lower arches can be accomplished sequentially, in any order, or simultaneously. As another example, upper arch 102 and lower arch 104 may be coupled subsequent to or prior to inserting upper arch 102 and lower arch 104 into the user's mouth. As another example, the adjustment of the forward position of lower arch 104 relative to upper arch 102 may be performed in measured increments interspersed with trial periods to test the effectiveness of the oral appliance in improving the user's breathing. Method 200 may include checking or verifying the forward position of lower arch 104 relative to upper arch 102 and then repeating step 208 as needed. The present invention contemplates using methods with additional steps, fewer steps, or different steps, so long as the methods remain appropriate for improving a user's breathing.

Although the present invention has been described in connection with several embodiments, it should be understood that a myriad of changes, substitutions, variations, alterations, transformations, and modifications may be suggested to one of skill in the art, and it is intended that the present invention encompass such changes, substitutions, variations, alterations, transformations, and modifications as fall within the spirit and scope of the appended claims.

What is claimed is:
1. An apparatus for use in treating a breathing condition, comprising:
   a first dental arch configured to receive at least some of a wearer's teeth;
   a second dental arch configured to receive at least some of a wearer's teeth;
   two bodies coupled to the first dental arch, each body comprising:
      a front stop;
      a rear stop;
      a threaded member coupled between the front stop and rear stop of the body and configured to rotate relative to the body; and
      a hook comprising:
         a threaded passage configured to engage the threaded member; and
         an arm configured to engage a second dental arch;

wherein the hook is configured to travel between the front stop and the rear stop of the body in response to rotational adjustment of the threaded member to adjust the lower dental arch relative to the upper dental arch; and two receivers coupled to the second dental arch, each receiver comprising a first rail configured to engage the arm of the hook of a respective one of the two bodies, the first rail being disposed exterior to an internal area defined by a span of the second dental arch;

wherein the two receivers are entirely disposed, with respect to each other, on opposite sides of a plane bisecting left and right halves of the second dental arch.

2. The apparatus of claim 1, wherein each receiver further comprises a second rail spaced apart from and substantially parallel to the first rail, the second rail configured to engage the aim of the hook of a respective one of the two bodies, and the second rail being disposed exterior to an internal area defined by the second dental arch.

3. The apparatus of claim 2, wherein each receiver comprises a cross bar coupling the first rail to the second rail, the cross bar being substantially perpendicular to the first and second rails.

4. The apparatus of claim 1, wherein each threaded member comprises an opening configured to receive a cooperatively shaped adjustment tool for rotational adjustment of the threaded member.

5. The apparatus of claim 4, wherein the first rail of each receiver comprises nickel-free stainless steel.

6. The apparatus of claim 1, wherein the first rail of each receiver has a maximum cross-sectional width that is greater than approximately 0.040 inches and less than approximately 0.100 inches.

7. The apparatus of claim 1, wherein the first rail of each receiver is coupled to the second dental arch at an angle substantially normal to the surface of the second dental arch where the first rail couples to the second dental arch.

8. The apparatus of claim 1, wherein the second dental arch is formed around at least a portion of each receiver.

9. The apparatus of claim 1, wherein each receiver is integrated into the second dental arch.

10. The apparatus of claim 1, wherein each body is integrated into the first dental arch.

11. The apparatus of claim 1, wherein each threaded member is configured to remain stationary in the forward direction in response to the rotational adjustment of the threaded member.

12. The apparatus of claim 1, wherein each body comprises a base, a front plate configured to be coupled to the base to provide the front stop, and a rear plate configured to be coupled to the base to provide the rear stop.

13. A method of improving a user's breathing, comprising:
inserting a first dental arch and a second dental arch into the user's mouth such that the first dental arch receives a first subset of the user's teeth and the second dental arch receives a second subset of the user's teeth, the first dental arch comprising two bodies, each body comprising:
a front stop;
a rear stop;
a threaded member coupled between the front stop and rear stop of the body and configured to rotate relative to the body; and
a hook comprising:
a threaded passage configured to engage the threaded member; and
an arm;

coupling the first dental arch to the second dental arch, the coupling comprising engaging the arm of each hook with a respective receiver, each receiver coupled to the second dental arch at a respective location exterior to an internal area defined by a span of the second dental arch; and adjusting the first dental arch relative to the second dental arch at least in part by rotating each of the threaded members of the two bodies.

14. The method of claim 13, wherein the adjusting further comprises:
inserting an adjustment tool into an opening of the threaded member; and
rotating the adjustment tool.

15. The method of claim 13, further comprising coupling a respective front plate to each of the bodies, each front plate providing the front stop for the body.

16. The method of claim 13, further comprising coupling a respective rear plate to each of the bodies, each rear plate providing the rear stop for the body.

17. The method of claim 13, further comprising coupling a rail of each receiver to the second dental arch at an angle substantially normal to the surface of the second dental arch where the rail couples to the second dental arch.

18. An apparatus for use in treating a breathing condition, comprising:
a first dental arch configured to receive at least some of a wearer's teeth;
a second dental arch configured to receive at least some of a wearer's teeth;
two bodies coupled to the first dental arch, each body comprising:
a base;
a front plate comprising a front stop, the front plate coupled to the base;
a rear plate comprising a rear stop, the rear plate coupled to the base;
a threaded member coupled between the front stop and rear stop of the body and configured to rotate relative to the body and to remain stationary in the forward direction in response to the rotational adjustment of the threaded member, the threaded member comprising an opening configured to receive a cooperatively shaped adjustment tool for rotational adjustment of the threaded member; and
a hook comprising:
a threaded passage configured to engage the threaded member; and
an arm configured to engage a second dental arch;
wherein the hook is configured to travel between the front stop and the rear stop of the body in response to rotational adjustment of the threaded member to adjust the lower dental arch relative to the upper dental arch; and two receivers coupled to the second dental arch, each receiver comprising a first rail configured to engage the arm of the hook of a respective one of the two bodies, and the first rail being disposed exterior to an internal area defined by a span of the second dental arch;

wherein the two receivers are entirely disposed, with respect to each other, on opposite sides of a plane bisecting left and right halves of the second dental arch.

19. The apparatus of claim 18, wherein each receiver further comprises a second rail spaced apart from and substantially parallel to the first rail, the second rail configured to engage the arm of the hook of a respective one of the two bodies, and the second rail being disposed exterior to an internal area defined by the second dental arch; and wherein each receiver comprises a cross bar coupling the first rail to the second rail, the cross bar being substantially perpendicular to the first and second rails.

20. The apparatus of claim 18, wherein the first rail of each receiver is coupled to the second dental arch at an angle substantially normal to the surface of the second dental arch where the first rail couples to the second dental arch.

21. An apparatus for use in treating a breathing condition, comprising:
   a first dental arch configured to receive at least some of a wearer's teeth;
   a second dental arch configured to receive at least some of a wearer's teeth;
   a first pair of positioning structures coupled to the first dental arch; and
   a second pair of positioning structures coupled to the second dental arch;
   wherein the first and second pairs of positioning structures are configured to engage each other in a manner that repositions the first dental arch in a forward direction relative to the second dental arch and in a manner that prevents sagittal separation between the and first and second dental arches beyond a fixed distance defined at least in part by the pair of positioning structures coupled to the first dental arch and the pair of positioning structures coupled to the second dental arch;
   wherein the first pair of positioning structures are disposed with respect to each other on opposite sides of a plane bisecting left and right halves of the first dental arch;
   wherein the second pair of positioning structures are disposed with respect to each other on opposite sides of a plane bisecting left and right halves of the second dental arch;
   wherein the first pair of positioning structures are located on the labial side of the first dental arch; and
   the second pair of positioning structures are located on the labial side of the second dental arch.

22. A method of improving a user's breathing, comprising:
   inserting a first dental arch and a second dental arch into the user's mouth such that the first dental arch receives a first subset of the user's teeth and the second dental arch receives a second subset of the user's teeth; and
   engaging a pair of positioning structures coupled to the first dental arch with a pair of positioning structures coupled to the second dental arch, the engaging comprising:
      positioning the first dental arch in a forward direction relative to the second dental arch; and
      preventing sagittal separation between the first and second dental arches beyond a fixed distance defined at least in part by the pair of positioning structures coupled to the first dental arch and the pair of positioning structures coupled to the second dental arch;
   wherein the first pair of positioning structures are disposed with respect to each other on opposite sides of a plane bisecting left and right halves of the first dental arch;
   wherein the second pair of positioning structures are disposed with respect to each other on opposite sides of a plane bisecting left and right halves of the second dental arch;
   wherein the first pair of positioning structures are located on the labial side of the first dental arch; and
   the second pair of positioning structures are located on the labial side of the second dental arch.

* * * * *